(12) United States Patent
Westermarck et al.

(10) Patent No.: US 9,062,309 B2
(45) Date of Patent: *Jun. 23, 2015

(54) USE OF A GROWTH-STIMULATING PROTEIN

(71) Applicant: Turun Yliopisto, Turun Yliopisto (FI)

(72) Inventors: Jukka Westermarck, Tampere (FI); Pietri Puustinen, Lieto (FI); Melissa Junttila, San Francisco, CA (US)

(73) Assignee: TURUN YLIOPISTO, Turun Yliopisto (FI)

( * ) Notice: Subject to any disclaimer, the term of this patent is extended or adjusted under 35 U.S.C. 154(b) by 80 days.

This patent is subject to a terminal disclaimer.

(21) Appl. No.: 13/849,210

(22) Filed: Mar. 22, 2013

(65) Prior Publication Data

US 2013/0197063 A1    Aug. 1, 2013

Related U.S. Application Data

(63) Continuation of application No. 13/246,696, filed on Sep. 27, 2011, now Pat. No. 8,410,072, which is a continuation of application No. 12/225,114, filed as application No. PCT/FI2007/050137 on Mar. 14, 2007, now abandoned.

(30) Foreign Application Priority Data

Mar. 16, 2006  (FI) .................................. 20060246

(51) Int. Cl.
| | | |
|---|---|---|
| C12N 15/113 | (2010.01) | |
| C07K 14/475 | (2006.01) | |
| G01N 33/574 | (2006.01) | |

(52) U.S. Cl.
CPC .......... *C12N 15/1136* (2013.01); *C07K 14/475* (2013.01); *C12N 15/113* (2013.01); *C12N 2310/14* (2013.01); *G01N 33/574* (2013.01); *G01N 33/57419* (2013.01); *G01N 2333/4706* (2013.01); *G01N 2500/02* (2013.01)

(58) Field of Classification Search
USPC ................... 435/6.11, 6.14, 91.1, 91.31, 455; 514/19.2, 44; 536/23.1, 24.5
See application file for complete search history.

(56) References Cited

U.S. PATENT DOCUMENTS

| 8,410,072 B2* | 4/2013 | Westermarck et al. ....... 435/455 |
|---|---|---|
| 2002/0086356 A1 | 7/2002 | Tuschl et al. |
| 2005/0255487 A1 | 11/2005 | Khvorova et al. |
| 2007/0275937 A1 | 11/2007 | Reading et al. |
| 2008/0113351 A1 | 5/2008 | Naito et al. |

FOREIGN PATENT DOCUMENTS

| WO | WO 02/44321 A2 | 6/2002 |
|---|---|---|
| WO | WO 02/081731 A2 | 10/2002 |
| WO | WO 2005/005601 A2 | 1/2005 |

OTHER PUBLICATIONS

Crooke, S., Ann. Rev. Medicine, vol. 55, pp. 61-95 (2004).*
Opalinska et al., Nature Rev., vol. 1, pp. 503-514 (2002).*
Perrachi et al., Rev. Med. Virol., vol. 14, pp. 47-64 (2004).*
Agrawal et al., Molecular Med. Today., vol. 6, pp. 72-81 (2000).*
Chirila et al., Biomaterials, vol. 23, pp. 321-342 (2002).*
Agrawal et al., "Antisense therapeutics: is it as simple as complementary base recognition?" Mol. Med. Today (2000) 6:72-81.
Chirila et al., "The use of syntheitc polymers for delivery of therapeutic antisense oligodeoxynucleotides" Biomaterials (2002) 23:321-42.
Crooke, Stanley T., "Progress in Antisense Technology" Annu. Rev. Med. (2004) 55:61-95.
Holen et al., "Positional effects of short Interfering RNAs targeting the human coagulation trigger Tissue Factor" Nucleic Acids Res. (2002) 30(8) :1757-1766.
Hoo et al., "Cloning and characterization of a novel 90 kDa 'companion' auto-antigen of p62 overexpressed in cancer" Oncogene (2002) 21:5006-15.
Hoo et al., "Identification and Charcterization of a Novel Cytoplasmic Autoantigen p90 in Human Gastric and Liver Cancer" Supplement to Molecular Biology of the Cell (2000) 11:357a, XP008110986.
Jang et al., "Gene delivery from polymer scaffolds for tissue engineering" Expert Rev. Medical Devices (2004) 1(1):127-38.
Opalinska et al., "Nucleic-Acid Therapeutics: Basic Principles and Recent Applications" Nature Review (2002) 1:503-12.
Peracchi, Alessio, "Prospects for antiviral ribozymes and deoxyribozymes" Rev. Med. Virol. (2004) 14:47-64.
Shi et al., "Preferential Humoral Immune Response in Prostate Cancer to Cellular Proteins p90 and p62 in a Panel of Tumor-Associated Antigens" The Prostate (2005) 63:252-58.
Shi, Fu-Dong, "Humoral immune response to p90 and other tumor-associated antigens in prostate cancer" Proceedings of the American Association for Cancer Research (2003) 44(2):360-61, XP001537187.

* cited by examiner

*Primary Examiner* — Jane Zara
(74) *Attorney, Agent, or Firm* — Birch, Stewart, Kolasch & Birch, LLP

(57) ABSTRACT

This invention relates to the inhibition of a newly discovered growth-stimulating protein in an individual. Further, the invention relates to a method for preventing or treating a cancer, or preventing or treating cancer growth, invasion or metastasis, or preventing or treating other hyperproliferative diseases in an individual, by down regulating the expression of said growth-stimulating protein or by inactivating said protein. Still further, the invention concerns a method for diagnosing cancer or other hyperproliferative diseases in an individual based on said growth-stimulating protein.

4 Claims, 10 Drawing Sheets

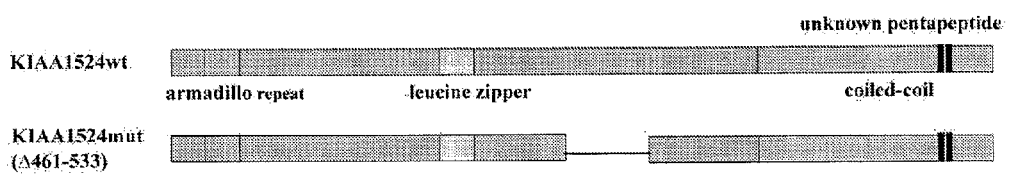

Fig. 2A

1 MDSTACLKSLLLTVSQYKAVKSEANATQLLRHLEVISGQKLTRLFTSNQILTSECLSCLVELLEDPNI
SASLILSIIGLLSQLAVDIETRDCLQNTYNLNSVLAGVVCRSSHTDSVFLQCIQLLQKLTYNVKIFYSGA
NIDELITFLIDHIQSSEDELKMPCLGLLANLCRHNLSVQTHIKTLSNVKSFYRTLITLLAHSSLTVVVFA
LSILSSLTLNEEVGEKLFHARNIHQTFQLIFNILINGDGTLTRKYSVDLLMDLLKNPKIADYLTRYEHFS
SCLHQVLGLLNGKDPDSSSKVLELLLAFCSVTQLRHMLTQMMFEQSPPGSATLGSHTKCLEPTVALLRWL
SQPLDGSENCSVLALELFKEIFEDVIDAANCSSADRFVTLLLPTILDQLQFTEQNLDEALTRKKCERIAK
SIEVLLTLCGDDTLKMHIAKILTTVKCTTLIEQQFTYGKIDLGFGTKVADSELCKLAADVILKTLDLINK
LKPLVPGMEVSFYKILQDPRLITPLAFALTSDNREQVQSGLRILLEAAPLPDFPALVLGESIAANNAYRQ
QETEHIPRKMPWQSSNHSFPTSIKCLTPHLKDGVPGLNIEELIEKLQSGMVVKDQICDVRISDIMDVYEM
KLSTLASKESRLQDLLETKALALAQADRLIAQHRCQRTQAETEARTLASMLREVERKNEELSVLLKAQQV
ESERAQSDIEHLFQHNRKLESVAEEHEILTKSYMELLQRNESTEKKNKDLQITCDSLNKQIETVKKLNES
LKEQNEKSIAQLIEKEEQRKEVQNQLVDREHKLANLHQKTKVQEEKIKTLQKEREDKEETIDILRKELSR
TEQIRKELSIKASSLEVQKAQLEGRLEEKESLVKLQQEELNKHSHMIAMIHSLSGGKINPETVNLSI 905

Fig. 2B

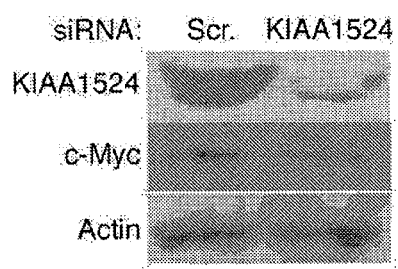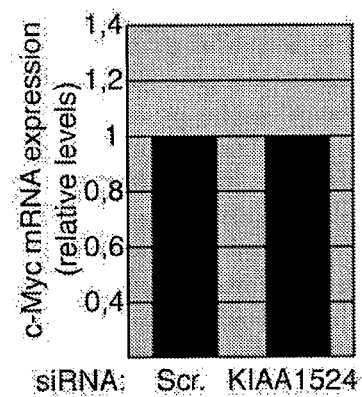
Fig. 4A                Fig. 4B
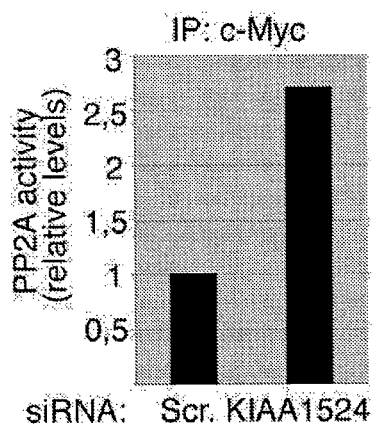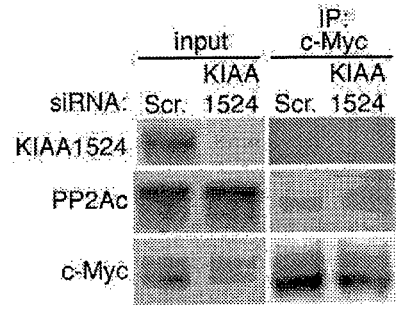
Fig. 4C                Fig. 4D

USE OF A GROWTH-STIMULATING PROTEIN

This application is a continuation of co-pending U.S. application Ser. No. 13/246,696, filed Sep. 27, 2011. U.S. application Ser. No. 13/246,696 is a continuation of U.S. application Ser. No. 12/225,114, filed Dec. 2, 2008. U.S. application Ser. No. 12/225,114 is the U.S. National Stage Application of PCT International Application No. PCT/FI2007/050137, filed Mar. 14, 2007, which claims the benefit of priority of Application No. 20060246, filed in Finland on Mar. 16, 2006. The entire contents of each of these applications are incorporated herein by reference.

FIELD OF THE INVENTION

This invention relates to the inhibition of a newly discovered growth-stimulating protein in an individual. Further, the invention relates to a method for preventing or treating a cancer, or preventing or treating cancer growth, invasion or metastasis, or preventing or treating other hyperproliferative diseases in an individual, by down regulating the expression of said growth-stimulating protein or by inactivating said protein. Still further, the invention concerns a method for diagnosing cancer or other hyperproliferative diseases in an individual based on said growth-stimulating protein.

BACKGROUND OF THE INVENTION

The publications and other materials used herein to illuminate the background of the invention, and in particular, cases to provide additional details respecting the practice, are incorporated by reference.

Cancer is a devastating disease afflicting all communities worldwide. It has been estimated that 1 out of 2 men and 1 out 3 women will develop some form cancer within their lifetime. It is also estimated that more than 550,000 people will die due to cancer in the United States alone during 2005. Cancer is a generalized term for a complex and vastly different set of diseases related to the uncontrolled growth, survival, and invasion of cells. Although there are more than 100 different types of cancer, as well as subtypes of each, recent studies have revealed limited number of genetic elements which are required for transformation of benign cells to cancer cells (Zhao et al., 2004). Generally, it has been concluded that human cell transformation requires activation of Ras GTPase, overexpression of telomerase, inactivation of tumor suppressor proteins p53 and Retinoblastoma protein (Rb) and inhibition of protein phosphatase 2A (PP2A) (Zhao et al., 2004). It is obvious that understanding of the function of these genetic elements could lead to development of cancer therapies that would be widely applicable to different types of cancer.

As described above, inhibition of PP2A activity has been identified as one of the prerequisites for transformation of primary human cells (Zhao et al., 2004). PP2A is a trimeric protein complex consisting of a catalytic subunit (PP2Ac or C), a scaffold subunit (PR65 or A) and one of the alternative regulatory B subunits (FIG. 1A) (Janssens and Goris, 2001). PP2A regulates cellular behaviour by dephosphorylating regulatory ser/thr residues of the protein kinases and other signaling proteins. Oncogenic transcription factor c-Myc is one of the many substrates for PP2A. It was recently shown, that PP2A-mediated dephosphorylation of serine 62 on c-Myc results in proteosomal degradation of the protein (Yeh et al., 2004). Importantly, viral small t-antigen, which inactivates PP2A, exerts its oncogenic potential by stabilization of c-Myc (Yeh et al., 2004).

Even though the importance of PP2A inhibition for human cell transformation has been firmly established by using viral antigens as research tools, the molecular mechanisms by which PP2A inhibition occurs in spontaneously transformed human cancer cells is currently not understood. There is thus an identified need of elucidating the mechanism by which PP2A inhibits transformation.

BRIEF DESCRIPTION OF THE INVENTION

This invention is based on the discovery of a growth-stimulating protein. The inventors of the present invention have found that the protein KIAA1524 (GenBank accession number AAI30565; SEQ ID NO.1) is an endogenous inhibitor of protein phosphatase 2A (PP2A) and that the protein KIAA1524 is required for tumor growth and cancer cell proliferation and that the protein KIAA1524 is up regulated in cancer tissue.

Thus, according to one aspect, this invention concerns a method for screening and identifying a therapeutic agent, which inhibits KIAA1524, said method comprising the steps of a) providing a first protein immobilized in a reaction chamber, b) adding a candidate agent and a labeled second protein to said chamber concomitantly or subsequently in any order, c) determining whether said first protein binds to said second protein, and d) identifying said candidate agent as a therapeutic agent inhibiting KIAA1524 when the determination in step c) is negative, wherein said first protein is KIAA1524 and said second protein is selected from the group consisting of PP2A, subunits thereof, and c-Myc, or vice versa.

According to another aspect, the invention concerns agents inhibiting KIAA1524, such as small interfering RNAs and peptides as described in the claims. Furthermore, the invention concerns pharmaceutical compositions comprising such agents.

According to a further aspect, the invention concerns a method for producing a pharmaceutical composition, said method comprising identifying an agent which inhibits KIAA1524 and mixing said agent with any suitable pharmaceutically acceptable expicient, as well as pharmaceutical compositions produced by such a method.

According to a further aspect, the invention concerns a method of inhibiting KIAA1524 in a human or animal patient in need thereof by administering a therapeutically effective amount of a pharmaceutical composition described in the claims.

According to a further aspect, the invention concerns use of an agent, which inhibits KIAA1524 for the manufacture of a pharmaceutical composition for treating, preventing and/or alleviating a disease selected from the group consisting of cancer and other hyperproliferative diseases.

According to a still further aspect, the invention concerns a method for determining the invasiveness of a malignant change in a mammal suspected to suffer from cancer, said method comprising: a) assessing the level of KIAA1524 expression in a sample, suspected to comprise malignant cells, taken from said mammal, b) comparing the expression level from step a) with the expression level of KIAA1524 in a non-malignant control sample, and c) determining said malignant changes as invasive when the expression level of KIAA1524 in said sample is significantly higher than the expression level of KIAA1524 in a non-malignant control sample.

BRIEF DESCRIPTION OF THE DRAWINGS

FIG. 1. KIAA1524 is an endogenous inhibitor of PP2A.

FIG. 2. KIAA1524 protein. FIG. 2A) Predicted structure of KIAA1524 protein reveals several putative protein-protein interaction domains. KIAA1524mut protein analyzed in FIGS. 1D and 1E. FIG. 2B) Amino acid sequence of the KIAA1524 protein (SEQ ID NO. 1).

FIG. 3. Identification of PP2A interacting domain in KIAA1524.

FIG. 4. KIAA1524 inhibits c-Myc associated PP2A activity and c-Myc degradation. FIG. 4A) siRNA-induced depletion of KIAA1524 protein results in downregulation of c-Myc protein expression in HeLa cells. FIG. 4B) siRNA-induced depletion of KIAA1524 protein does not inhibit c-Myc mRNA expression. FIG. 4C) siRNA-induced depletion of KIAA1524 protein enhances PP2A activity in c-Myc immunoprecipitates. FIG. 4D) KIAA1524 protein does not regulate interaction between PP2Ac and c-Myc proteins. HeLa cells transfected with either scrambled or KIAA1524 siRNA were subjected to co-immunoprecipitation analysis with c-Myc specific antibody. Proteins in the immunoprecipitates were thereafter studied by indicated antibodies.

FIG. 5. Identification of KIAA1524 interacting domain in c-Myc.

FIG. 6E) siRNA-induced depletion of KIAA1524 protein inhibits HeLa cell anchorage independent growth on agar.

FIG. 7. KIAA1524 is overexpressed in human squamous cell carcinomas of the head and neck (HNSCC).

FIG. 8. KIAA1524 is overexpressed in human colon cancers.

FIG. 9. KIAA1524 is overexpressed in human breast cancers.

DETAILED DESCRIPTION OF THE INVENTION

Figure 1A:
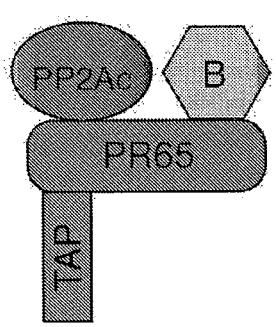
FIG. 1A) shows a schematic picture of the PP2A complex containing PR65 scaffold, PP2Ac catalytic subunit and a regulatory B-subunit. TAP-fusion of the PR65 protein used in the TAP-purification is shown.

The present invention is based on identification of KIAA1524 as a growth-stimulating protein, which interacts with PP2A and inhibits the tumor suppressor activity thereof.

The present invention thus provides KIAA1524 as a target for novel anticancer or antiproliferative agents.

KIAA1524 was identified as a PP2A interacting protein based on co-immunoprecipitation with PR65 protein, a scaffolding subunit of PP2A protein complex, and subsequent mass-spectrometric peptide sequencing. The ability of KIAA1524 to interact with PP2A complex was demonstrated by co-immunoprecipitation analysis of endogenous PR65 proteins and by using deletion mutants of KIAA1524. In addition the functional role of KIAA1524 as PP2A inhibitor was demonstrated by depleting KIAA1524 by short interfering RNA (siRNA) oligos targeted to KIAA1524, which resulted in stimulation of PP2A phosphatase activity.

Furthermore, based on co-immunoprecipitation experiments, KIAA1524 was identified as a protein directly interacting with transcription factor c-Myc. Said interaction was shown to stabilize c-Myc protein thereby promoting its oncogenic potential.

The role of KIAA1524 in regulation of cancer cell behavior was studied e.g. by transfecting cells with KIAA1524 siRNA and subsequently determining cell proliferation both in a cell culture and in an in vivo mouse model. Depletion of KIAA1524 resulted in inhibition of cell proliferation and inhibition of anchorage independent growth of the cells, as well as compromised tumor formation in mice. Furthermore, KIAA1524 was found to be overexpressed in human malignancies, such as head and neck squamous cell carcinoma (HNSCC), colon cancer and breast cancer. Especially KIAA1524 overexpression was found in invasive tumors of colon cancer and breast cancer when compared to non-invasive tumors of the same origin. These and other results disclosed below indicate that KIAA1524 promotes cancer cell growth and therefore KIAA1524 serves as a target for cancer therapeutics.

The present invention is directed to a method for screening and identifying a therapeutic agent which inhibits KIAA1524 and is thus useful in treating, preventing and/or alleviating cancer, cancer cell proliferation, invasion, metastasis, as well as other hyperproliferative diseases, such as psoriasis, myocardial hypertrophy and benign tumor, such as adenoma, hamartoma and chondroma.

As used throughout this specification, the term "inhibiting KIAA1524" includes down-regulating the expression of KIAA1524, inhibiting the activity of KIAA1524, inactivating KIAA1524, as well as inhibiting KIAA1524 interaction with PP2A complex or c-Myc. The words inhibit and block, are used interchangeably.

The above method comprises the following steps: a) providing a first protein immobilized in a reaction chamber, b) adding a candidate agent and a labeled second protein to said chamber concomitantly or subsequently in any order, c) determining whether said first protein binds to said second protein, and d) identifying said candidate agent as a therapeutic agent inhibiting KIAA1524 when the determination in step c) is negative but positive in the absence of a therapeutic agent. In the method, said first protein is KIAA1524 and said second protein is selected from PP2A, subunits thereof, i.e. PP2Ac α or β, PR65α or β, or any of the alternative B-subunits (B, B', B"), and c-Myc, or vice versa.

Immobilization of said first protein to a reaction chamber, such as a multi-well plate, can be performed by any suitable method known in the art. Such methods are apparent to a person skilled who also appreciates how to immobilize said protein without affecting its conformation or binding properties.

Any suitable labels and labeling methods known in the art can be used for labeling said second protein. Preferably, said label is a fluorescent label, such as green fluorescent protein or chemical fluorescent label such as Texas red. The said label can also be a protein such as firefly luciferase that emit light when incubated with a substrate such as luciferin. In addition the said label can be an enzyme such as horse-radish peroxidase that produces a colorimetric reaction when incubated with its substrate such as 3-amino,9-ethyl-carbazole.

Determination of whether said first protein binds to said second protein in the presence of the candidate agent can be performed by any suitable method depending on the label used. For example, if fluorescent label is used, protein binding can be determined by optical instrument composed of a light source which is preferably a laser and a sensor that detects the light emitted from fluorescent label in response to excitation by light or laser. In the case of colorimetric reaction, such as is the case when for example horse-radish peroxidase label is used in combination with its substrate such as 3-amino,9-ethyl-carbazole, protein binding can be determined by change in the absorbance of light in the wavelength range of interest.

It will be apparent to a person skilled in the art that the method may also contain various additional steps, such as incubations and washings. For example, washing may be required after step b) to remove unbound second protein.

In one embodiment according to the present invention, the method can be used for a high-throughput screening of inhibitors of protein-protein interactions by immobilizing a first protein, or a target protein, on a 96, 384 well or any equivalent multi-well plate and incubating that with a second protein fused to for example green fluorescent protein, Texas red or luciferase protein. Using a plate reader the light emitted by the fluorescent label is measured and the in a case of interaction the light signal is detected from a well. Combining such assay with peptide and small molecule compound libraries will allow identification of potential drug-like molecules that inhibit protein interaction, detected by loss of fluorescence signal in the chamber.

The present invention is further directed to a method for producing a pharmaceutical composition, said method comprising identifying an agent which inhibits KIAA1524 and mixing said agent with any suitable pharmaceutically acceptable expicient well known to a person skilled in the art. In one embodiment, said identification is performed using the screening and identification method disclosed above.

Furthermore, the present invention is directed to a method of inhibiting KIAA1524 in a human or animal patient in need thereof by administering a therapeutically effective amount of a pharmaceutical composition produced according to the present invention.

It is believed that this method can be useful for treating any cancer. However, this method is especially suitable for treating or preventing of cancers located in certain tissues and cancers that would be difficult or impossible to treat by surgery or radiation. As an example of such cancers, can be mentioned squamous cell carcinomas of the head and neck, colon cancer and breast cancer.

It is believed that this method can be also useful for treating hyperproliferative disease in which KIAA1524 is expressed. An example of such diseases psoriasis, myocardial hypertrophy and benign tumor, such as adenoma, hamartoma and chondroma.

The method according to this invention can be accomplished either as the sole treating or preventing method, or as an adjuvant therapy, combined with other methods such as administration of cytotoxic agents, surgery, radiotherapy, immunotherapy etc.

Agents that may be identified according to various embodiments according to the present invention and/or are useful in the methods according to the present invention include, but are not limited to, oligonucleotides, such as antisense oligonucleotide, siRNA and ribozyme molecule, a peptide, a peptidomimetic, a chemical compound, a small molecule, an antibody raised against said KIAA1524, and an aptamer (an oligonucleotide) affecting the protein conformation of KIAA1524 resulting in the inactivation of the same.

According to a preferable embodiment, said agent is an agent down-regulating the expression of KIAA1524.

According to one preferable embodiment, the down regulation of the KIAA1524 is possible, for example, by use of an antisense oligonucleotide, modified nucleotide, sequence of combination of different kinds of nucleotides to prevent or modify the KIAA1524 synthesis. The antisense oligonucleotide can be a DNA molecule or an RNA molecule.

Ribozymes cleaving the KIAA1524 mRNA are also included. The ribozyme technology is described for example in the following publication: Ribozyme technology for cancer gene target identification and validation. Li et al., Adv. Cancer Res. 2007; 96:103-43. Also small interfering RNA molecules (siRNAs) would be useful. The application of siRNA:s has become important in the development of new therapies in the last years. O Heidenreich presents an overview of pharmaceutical applications in the article "Forging therapeutics from small interfering RNAs in European Pharmaceutical Review Issue 1, 2005. The principle has particularly been suggested for the treatment of tumors and carcinomas, sarcomas, hypercholesterolemia, neuroblastoma and herpetic stromal keratitis.

The principle of siRNA is extensively presented in literature. As examples can be mentioned the US patent publications 2003/0143732, 2003/0148507, 2003/0175950, 2003/0190635, 2004/0019001, 2005/0008617 and 2005/0043266. An siRNA duplex molecule comprises an antisense region and a sense strand wherein said antisense strand comprises sequence complementary to a target region in an mRNA sequence encoding a certain protein, and the sense strand comprises sequence complementary to the said antisense strand. Thus, the siRNA duplex molecule is assembled from two nucleic acid fragments wherein one fragment comprises the antisense strand and the second fragment comprises the sense strand of said siRNA molecule. The sense strand and antisense strand can be covalently connected via a linker molecule, which can be a polynucleotide linker or a non-nucleotide linker. The length of the antisense and sense strands are typically about 19 to 21 nucleotides each. However, also synthetic double-stranded RNA (dsRNA) Dicer substrate duplexes 25-30 nucleotides in length, which has been recently reported to be more potent than corresponding conventional 21-mer small interfering RNAs (siRNAs) (Kim et al., 2005), can be used. Typically, the antisense strand and the sense strand both comprise a 3'-terminal overhang of a few, typically 2 nucleotides. The 5'-terminal of the antisense is typically a phosphate group (P). The siRNA duplexes having terminal phosphate groups (P) are easier to administrate into the cell than a single stranded antisense. In the cell, an active siRNA antisense strand is formed and it recognizes a target region of the target mRNA. This in turn leads to cleaving of the target RNA by the RISC endonuclease complex (RISC=RNA-induced silencing complex) and also in the synthesis of additional RNA by RNA dependent RNA polymerase (RdRP), which can activate DICER and result in additional siRNA duplex molecules, thereby amplifying the response.

One of the challenges related to small interfering RNAs is the identification of a potent siRNA for the corresponding mRNA. It should be noted that genes with incomplete complementarity are inadvertently downregulated by the siRNA, leading to problems in data interpretation and potential toxicity. This however can be partly addressed by carefully designing appropriate siRNAs with design algorithms. These computer programs sieve out given target sequence with a set of rules to find sequence stretches with low GC content, a lack of internal repeats, an A/U rich 5-end and high local free binding energy which are features that enhance the silencing effect of siRNA.

In order to identify agents useful in the present invention, several different KIAA1524 siRNAs were designed by using commercial and non commercial algorithms. To this end, full length cDNA sequence of KIAA1524 (GenBank accession number NM_020890) was loaded to siRNA algorithm programs (http://www.mwg-biotech.com/html/s_synthetic_acids/s_sirna_design.shtml) and stand alone program developed by: Wenwu Cuia, Jianchang Ningb, Ulhas P. Naika, Melinda K. Duncana, (OptiRNAi, an RNAi design tool. Computer Methods and Programs in Biomedicine (2004) 75, 67-73). Further, algorithm generated siRNA sequences were then screened trough genome wide DNA sequence alignment (BLAST) (http://www.ncbi.nlm.nih.gov/blast) to eliminate siRNAs which are not free from off-targeting. In other words, all those siRNAs which had even short sequence regions matching with other genes than target gene (KIAA1524) were considered invaluable for further use. This approach resulted in identification of 5 potential siRNAs depicted in SEQ ID NO:s 2 to 6.

Obtained siRNAs were then transfected to different cell lines and their capacity to degrade mRNA and further deplete translation of KIAA1524 was studied at protein level by measuring the amount of KIAA1524 protein after siRNA treatment with KIAA1524 specific antibodies. Those siRNA sequences giving the strongest downregulation of KIAA1524 protein at the lowest concentration used are marked with an asterisk in Table 1.

TABLE 1

Efficiency of siRNAs to Downregulate KIAA1524 Expression

| SEQ ID NO | Sequence | Length | Efficiency |
|---|---|---|---|
| 2 | AACATCAGTGCTTCACTGATCCTT | 24 | Moderate |
| 3 | AACTGTGGTTGTGTTTGCACTTT | 23 | High * |
| 4 | GGUUGCAGAUUCUGAAUUAUU | 21 | Moderate |
| 5 | AAUGCCUUGUCUAGGAUUAUU | 21 | Low |
| 6 | ACCAUUGAUAUCCUUAGAAUU | 21 | High * |

The present invention thus concerns KIAA1524 siRNAs selected from the group consisting of SEQ ID NO:s 2 to 6 and their use as pharmaceuticals. Preferable siRNAs depicted in SEQ ID NO:s 2 and 4, and more preferable siRNAs depicted in SEQ ID NO:s 3 and 6 are provided. It is obvious that in some applications said siRNAs may be longer than 21-25 nucleotides or dsRNA dicer substrate duplexes.

The oligonucleotide (such as antisense, siRNA or ribozyme molecule) shall, when used as a pharmaceutical, be introduced in a target cell. The delivery can be accomplished in two principally different ways: 1) exogenous delivery of the oligonucleotide or 2) endogenous transcription of a DNA sequence encoding the oligonucleotide, where the DNA sequence is located in a vector.

Normal, unmodified RNA has low stability under physiological conditions because of its degradation by ribonuclease enzymes present in the living cell. If the oligonucleotide shall be administered exogenously, it is highly desirable to modify the molecule according to known methods so as to enhance its stability against chemical and enzymatic degradation.

Modifications of nucleotides to be administered exogenously in vivo are extensively described in the art. Principally, any part of the nucleotide, i.e the ribose sugar, the base and/or internucleotidic phosphodiester strands can be modified. For example, removal of the 2'-OH group from the ribose unit to give T-deoxyribosenucleotides results in improved stability. Prior disclosed are also other modifications at this group: the replacement of the ribose 2'-OH group with alkyl, alkenyl, allyl, alkoxyalkyl, halo, amino, azido or sulfhydryl groups. Also other modifications at the ribose unit can be performed: locked nucleid acids (LNA) containing methylene linkages between the 2'- and 4'-positions of the ribose can be employed to create higher intrinsic stability.

Furthermore, the internucleotidic phosphodiester linkage can, for example, be modified so that one or more oxygen is replaced by sulfur, amino, alkyl or alkoxy groups. Also the base in the nucleotides can be modified.

Preferably, the oligonucleotide comprises modifications of one or more 2'-hydroxyl groups at ribose sugars, and/or modifications in one or more internucleotidic phosphodiester linkages, and/or one or more locked nucleic acid (LNA) modification between the 2'- and 4'-position of the ribose sugars.

Particularly preferable modifications are, for example, replacement of one or more of the 2'-OH groups by 2'-deoxy, 2'-O-methyl, 2'-halo, eg. fluoro or 2'-methoxyethyl. Especially preferred are oligonucleotides where some of the internucleotide phoshodiester linkages also are modified, e.g. replaced by phosphorothioate linkages.

It should be stressed that the modifications mentioned above are only non-limiting examples.

According to one preferable embodiment, the agent identifiable by the screening assay or useful in the method according to the present invention prevents or inhibits tumor growth and proliferation by inhibiting said KIAA1524 from interacting with PP2A complex or with transcription factor c-Myc. Alternatively, said agent inhibits KIAA1524 growth and proliferation enhancing effects that are not dependent on KIAA1524 interaction with PP2A or c-Myc. Said agent can, for example, be a peptide, peptidomimetic, a small molecule, an antibody raised against said KIAA1524, or an aptamer (an oligonucleotide) affecting the protein conformation of KIAA1524 resulting in the inactivation of the same.

Results from PR65 co-immunoprecipitation experiments showed that KIAA1524 interacts both with PR65 and PP2Ac subunits of PP2A protein complex. In order to identify the region in KIAA1524 that mediates the protein-protein interaction, it was studied whether deletion of any region in the KIAA1524 protein would abrogate its association with PP2A. To this end, a series of KIAA1524 deletion constructs with each deletion corresponding to approximately 50-100 amino acids of the protein coding sequence were generated and transiently transfected into HeLa cells. Out of the eleven KIAA1524 deletions, KIAA1524 lacking the amino acids between 461-533 was the only mutant that in repetitive experiments showed impaired binding to PR65 as demonstrated by co-immunoprecipitation experiments. Thus, the region ranging from amino acid 461 to amino acid 533 in SEQ ID NO. 1 is a particularly important target for novel cancer therapeutics.

Thus, according to a particularly preferred embodiment, the agent inactivates the KIAA1524 in the region ranging from aa 461 through 533 or any other region on KIAA1524 that participates on interaction between PP2A complex and KIAA1524 protein. Said agent can, for example, be a peptide, a peptidomimetic, a small molecule, an antibody raised against said KIAA1524, or an aptamer (an oligonucleotide) affecting the protein conformation of KIAA1524 resulting in the inactivation of the same.

More specifically, the present invention provides blocking peptides comprising any stretch of 3 to 60 amino acids, preferably 3 to 30, preferably 6 to 18, preferably 6 to 12, or preferably 9 to 12 amino acids corresponding to the amino acids of the region aa 461-533 of KIAA1524 depicted in SEQ ID NO. 1. It is obvious that in some applications said blocking peptides may be longer that 60 amino acids. Peptides according to the present invention bind to PP2A complex components and inhibit the interaction between KIAA1524 and PP2A thereby eliciting the tumor suppressor activity of PP2A, and on the other hand, inhibiting or blocking KIAA1524. In other embodiments according to the present invention, said blocking peptides comprise at least one, preferably 1 to 20, preferably 1 to 10, preferably 2 to 6, preferably 2 to 4, or preferably 3 to 4 consecutive sequences selected from the group consisting of SEQ ID NO:s 7 to 30 and conservative sequence variants thereof.

Figure 3A:
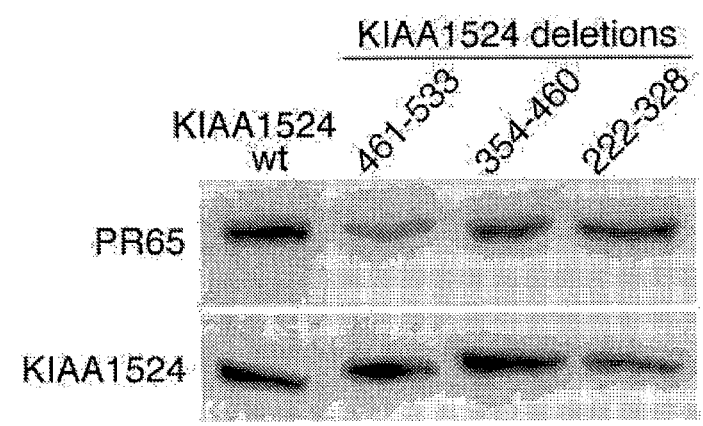
FIG. 3A) Co-immunoprecipitation of the KIAA1524 deletion constructs with endogenous PR65 from HeLa cell lysates. Co-immunoprecipitation of indicated Flag-KIAA1524 proteins and the PP2A complex was analyzed by western blotting of the anti-Flag immunoprecipitates with the PR65 antibody Immunoprecipitation efficiency of the KIAA1524 deletions was confirmed by KIAA1524 immunoblotting.
Figure 3B:
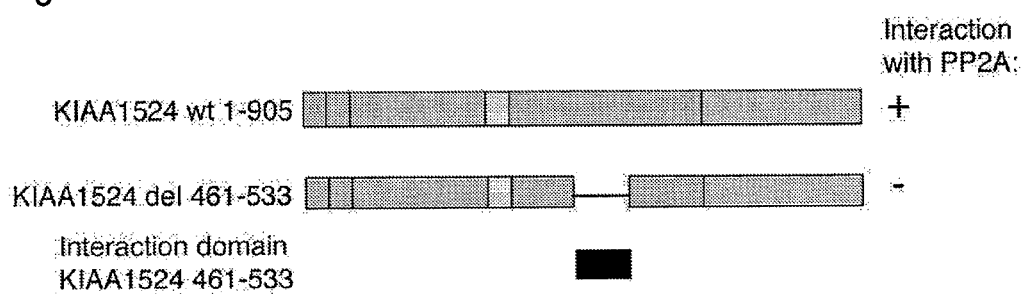
FIG. 3B) Identification of putative PP2A-interacting domain in KIAA1524. Results in FIG. 3A show that wild-type KIAA1524 interacts with PP2A (PR65), whereas KIAA1524 in which 461-533 domain is deleted displays impaired interaction with PP2A. Therefore, the KIAA1524 domain 461-533 is expected to mediate interaction between KIAA1524 and PP2A.

In order to study whether depletion of KIAA1524 affects the functional interaction of the PP2A complex with its substrate c-Myc, steady-state expression level of c-Myc was studied in HeLa cell extracts after transfection with KIAA1524 siRNA. As shown in FIG. 3A, siRNA-induced depletion of KIAA1524 resulted in down-regulation of c-Myc protein expression in HeLa cells, while, as demonstrated in FIG. 3B, c-Myc mRNA expression was not affected. These results indicated KIAA1524 regulates c-Myc protein levels post-transcriptionally. To study if the decrease in c-Myc protein levels was caused by protein destabilization, the effect of KIAA1524 depletion on the half-life of endogenous c-Myc protein was examined by pulse-chase analysis. As described in more detail in the Experimental Section, KIAA1524 depletion significantly reduced c-Myc protein stability thus indication that KIAA1524 is an important regulator of c-Myc stability.

Co-immunoprecipitation of c-Myc and KIAA1524 from cellular extracts demonstrated a physical association between these proteins (FIG. 3D). To elucidate the interaction between KIAA1524 and c-Myc further, full-length Flag-tagged recombinant KIAA1524 was produced in insect cells and an in vitro protein-protein interaction assay with recombinant GST-fused amino terminal portion of c-Myc (amino acids 1-262 of the sequence under GenBank accession number NP_002458) was performed. Results indicated that GST-c-Myc 1-262 interacts with KIAA1524, whereas proteolytic degradation fragment of GST-Myc 1-262, corresponding to size of GST-Myc 1-120 does not interact with KIAA1524. Therefore, the c-Myc domain 120-262 is expected to mediate direct binding of c-Myc to KIAA1524. Said c-Myc domain 120-262 contains 143 amino acids and corresponds to amino acids 1-143 depicted in SEQ ID NO. 31.

The present invention thus provides blocking peptides, which are useful in inhibiting the interaction of KIAA1524 and c-Myc. In one particular embodiment, blocking peptides comprising any stretch of 3 to 60 amino acids, preferably 3 to 30, preferably 6 to 18, preferably 6 to 12, or preferably 9 to 12 amino acids, corresponding to the amino acids 1-143 depicted in SEQ ID NO. 31, and inhibiting KIAA1524 are provided. Said binding results in inhibition of the interaction between KIAA1524 and c-Myc thereby inhibiting or blocking the KIAA1524. In other embodiments according to the present invention, said blocking peptides comprise at least one, preferably 1 to 20, preferably 1 to 10, preferably 2 to 6, preferably 2 to 4, or preferably 3 to 4 consecutive sequences selected from the group consisting of SEQ ID NO:s 32 to 79, and conservative sequence variants thereof.

In order to test the blocking ability of the peptides according to the present invention, said peptides are administered to cells, such as HeLa cancer cells, and, depending on the nature of the peptides, either a) their ability to prevent binding of KIAA1524 to PP2A or b) their ability to prevent binding of KIAA1524 to c-Myc is detected by any suitable method, such as immunoprecipitation analysis of KIAA1524-PP2A interaction or by western blot analysis of cellular lysates using antibodies specific for c-Myc serine 62 phosphorylation. Peptides, which prevent said binding to a statistically significant extent, are considered as blocking peptides.

By the term "conservative sequence variant" it is meant herein variants arising from amino acid sequence modifications, which do not significantly alter the binding properties of the peptides according to the present invention. Such modifications are apparent to a person skilled in the art, and they include amino acid sequence variants arising from amino acid substitutions with similar amino acids, as well as amino acid deletions and additions. With respect to longer peptides according to the present invention, such as peptides comprising more than 9 amino acids, preferably more than 12, preferably more than 12, preferably more than 18, or preferably more than 30 amino acids, the present invention includes those, which have at least 90% identity, or at least 95%, 96%, 97%, 98% or 99% identity to the polypeptides described above.

When used as a pharmaceutical, blocking peptides according to the present invention may be administered by any suitable way, such as intravenous injection, intraperitoneal injection, and intrathecal injection. In one embodiment, blocking peptides are fused to cell penetrating peptides (CPPs) known in the art, which deliver the fusion peptides across the cell membrane. Such fusion peptides may be administered e.g. by as intravenous injection, intraperitoneal injection, and intrathecal injection. It will be obvious to a person skilled in the art that, as the technology advances, that blocking peptides and fusion peptides according to present invention may be administrated by any other suitable way or route of administration.

In addition to the present finding that KIAA1524 is overexpressed in human cancer tissues, such as HNSCC, colon cancer and breast cancer, it was found that the KIAA1524 expression level correlates with the tumor gradus. For example, malignant subtypes of breast cancer expressed statistically significantly more KIAA1524 than benign subtypes. Furthermore, colon cancers with higher tumor gradus expressed statistically significantly more KIAA1524 than colon cancers with lower gradus.

This invention concerns also a method for diagnosing cancer or hyperproliferative disease, based on detecting or quantifying the level of the KIAA1524 protein in a tissue or body fluid by i) determining the KIAA1524 mRNA expression from said tissue or body fluid by RT-PCR, or by a hybridizing technique, or ii) subjecting the tissue or body fluid expected to contain the protein KIAA1524 to an antibody recognizing said KIAA1524, and detecting and/or quantifying said antibody, or subjecting said tissue or body fluid to analysis by proteomics technique.

The hybridizing technique include, for example DNA hybridization and northern blot. The detection or quantification of the antibody can be performed according to standard immunoassay protocols, such as label-linked immunosorbent assays, western blot and immunohistochemical methods.

This invention concerns also a method for diagnosing cancer or hyperproliferative disease, based on detecting or quantifying the mutations or single nucleotide polymorphisms in KIAA1524 gene by hybridizing technique or by DNA or RNA sequencing or by RT-PCR analysis of the RNA or DNA.

The diagnosis can be carried out by KIAA1524 alone or with the same in combination with other proteins or genes.

More specifically, the present invention concerns a method for determining the invasiveness of a malignant change in a mammal suspected to suffer from cancer, said method comprising a) assessing the level of KIAA1524 expression in a sample, suspected to comprise malignant cells, taken from said mammal, b) comparing the expression level from step a) with the expression level of KIAA1524 in a non-malignant control sample, and c) determining said malignant change as invasive, when the expression level of KIAA1524 in said sample is significantly higher than the expression level of KIAA1524 in a non-malignant control sample. Preferably, the expression level of KIAA1524 in said sample is more than 2, preferably more than 3 times higher than in said control sample.

In one embodiment according to the present invention, the above method is used for determining the gradus of a malignant change in a mammal suspected to suffer from cancer, such as colon cancer, by determining in step c) the gradus of said malignant change as gradus III or IV, when the expression level of KIAA1524 is significantly higher than the expression level of KIAA1524 in a non-malignant control sample or in a non-invasive gradus I and II sample. Furthermore, the present invention provides a method for distinguishing invasive and metastazing gradus III and IV from non-invasive and non-metastazing gradus II in cases where said expression level is more than 2 and preferably 3 times higher than in gradus II or in a non-malignant control sample.

In a further embodiment according to the present invention, the above method is used for distinguishing invasive tumor types of breast cancer, such as invasive ductal carcinoma (IDC), invasive lobular carcinoma (ILC) and IDC with intraductal comedo carcinoma (IDC+ICC), from mucinous carcinomas in cases where the expression level of KIAA1524 is more than 2, preferably more than 3 times higher than in a non-malignant control sample.

The invention will be illuminated by the following non-restrictive Experimental Section.

Experimental Section

Results
Identification of KIAA1524

Figure 1B:
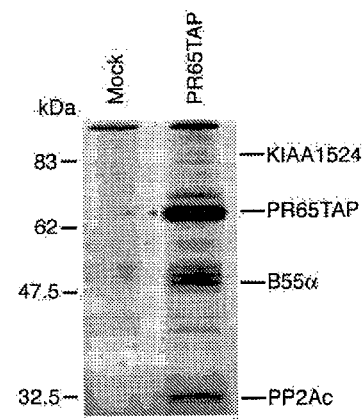
FIG. 1B) TAP purification of the PR65 protein complex from HT-1080 fibrosarcoma cells. Proteins in the PR65TAP eluates were identified by mass-spectrometric peptide sequencing.

To identify PP2A interacting proteins from HT-1080 cells we generated cell clones stably overexpressing TAP-tagged PR65 protein, a scaffolding subunit of the PP2A complex (FIG. 1A). TAP purification of cytoplasmic extracts of either mock transfected control or PR65TAP expressing cells revealed several proteins that co-purify with PR65TAP but were not present in the final eluates from the control cells (FIG. 1B). Several of these putative PR65 interacting proteins were subsequently identified by mass-spectrometric peptide sequencing. Among the proteins identified from the PR65TAP complex are both the catalytic subunit (PP2Ac) and PP2A B-subunits, thus validating the approach (FIG. 1B). In addition, we were able to identify KIAA1524 as a novel putative PP2A associated protein. KIAA1524 is a 90 kDA cytoplasmic protein with no previously identified cellular function (FIG. 2) (Soo Hoo et al., 2002). Results presented below, identify KIAA1524 as an endogenous inhibitor of PP2A specifically up-regulated in cancer.

Figure 1C:
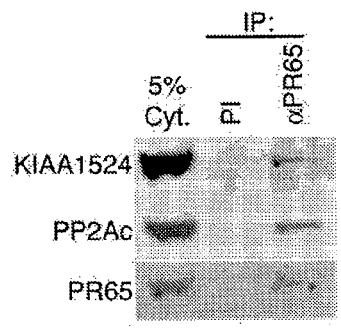
FIG. 1C) Co-immunoprecipitation analysis of HeLa cell cytoplasmic extracts with PR65 antibody reveals interaction between endogenous KIAA1524, PR65 and PP2Ac proteins. PI, pre-immune serum; input, input material.
Figure 1D:
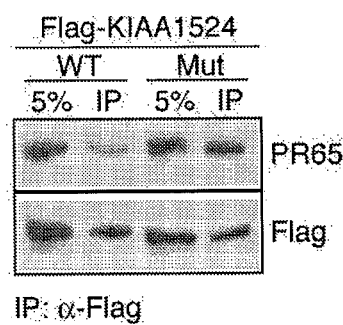
FIG. 1D) Identification of a mutant of KIAA1524 protein deficient in PR65 binding by co-immunoprecipitation analysis.

Results from PR65 co-immunoprecipitation analysis show that endogenous KIAA1524 interacts with endogenous PR65 and PP2Ac (FIG. 1C). In order to identify the region in KIAA1524 that mediates the protein-protein interaction between KIAA1524 and PP2A complex, we have constructed a series of cDNA constructs coding for KIAA1524 deletion mutants. To this end, a series of Flag-tagged KIAA1524 deletion constructs were transiently transfected into HeLa cells for 48 h, followed by immunoprecipitation with anti-Flag antibody. Interaction between the KIAA1524 mutants and the PP2A complex was assessed by Western blot analysis of the PR65 subunit. Immunoprecipitation of Flag-KIAA1524 wild-type (KIAA1524wt) (FIG. 2A) construct revealed a clear interaction with endogenous PR65 protein (FIGS. 1D and 3A). Interaction occurred in both low (150 mM NaCl) or moderate (300 mM NaCl) stringency conditions. However, a mutant of KIAA1524, lacking the amino acids between 461-533 (KIAA1524mut) (FIG. 2A), displayed greatly reduced interaction with PR65 (FIGS. 1D and 3A). KIAA1524mut was the only mutant out of eleven deletion mutants that demonstrated impaired binding to PR65 in either stringency condition.

Figure 1E:
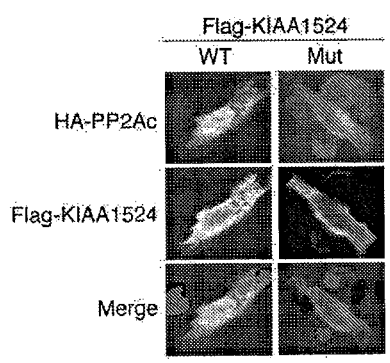
FIG. 1E) HeLa cells transfected with indicated expression constructs were analyzed by confocal microscopy for KIA1524-PP2Ac co-localization.
Figure 1F:
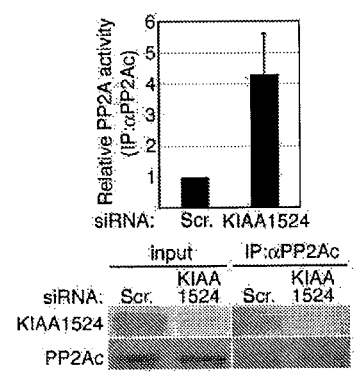
FIG. 1F) siRNA-mediated depletion of KIAA1524 protein expression in HeLa cells enhances serine/threonine phosphatase activity of immunoprecipitated PP2Ac.

Next we studied the co-localization of PP2Ac and KIAA1524 from cells co-transfected with either KIAA1524 wt or KIAA1524mut constructs together with HA-PP2Ac. As shown in FIG. 1E, confocal image analysis of transfected cells revealed co-localization with PP2Ac and KIAA1524 wt, whereas no co-localization was observed with PP2Ac and KIAA1524mut (FIG. 1E). In order to study the role of KIAA1524 in the regulation of PP2A function, we have inhibited KIAA1524 expression in HeLa cells using short interfering RNA (siRNA) oligos. Importantly, depletion of KIAA1524 expression by siRNA stimulated PP2A phosphatase activity as measured from the PP2Ac immunoprecipitates (FIG. 1F). Taken together these results demonstrate that KIAA1524 interacts with and inhibits the catalytic activity of the PP2A complex in cultured cells. Moreover, the data show that the interaction is stable at moderate ionic strength and that amino acids 461-533 of KIAA1524 contain the PP2A interaction domain of KIAA1524.

KIAA1524 Promotes c-Myc Protein Stability

To probe for the uncharacterized cellular functions of KIAA1524, genome-wide gene expression profiles of scrambled and KIAA1524 siRNA transfected HeLa cells were compared after 72 h. Remarkably, only a minor fraction of genes (76 out of 26091) included in the Sentrix® Human-6 Expression BeadChip (Illumina Inc.), showed a reproducible and statistically significant ($p<0.05$, data not shown) difference in their expression levels between scrambled and KIAA1524 siRNA transfected cells (FIG. 1F). PP2A activity has been shown to regulate the activity of two transformation relevant transcription factors, p53 and c-Myc. To characterize these two transcription factors in relation to the transcriptional profile of KIAA1524 depleted cells, the list of 76 genes affected by KIAA1524 depletion was compared to target gene databases published for p53 and c-Myc. Based on a p53 target gene database (http://p53.bii.a-star.edu.sg/aboutp53/targetgene/index.php), only 1/76 genes affected by KIAA1524 depletion has been published to harbor a p53 binding site in its promoter or to be transcriptionally regulated by p53. However, when compared with a c-Myc target gene database (http://www.myc-cancer-gene.org/site/mycTargetDB.asp), 16% (12/76) of genes affected by KIAA1524 depletion were found to bind c-Myc in their promoter region. These findings, together with the published role of PP2A regulation of c-Myc protein stability, suggest that KIAA1524 may regulate c-Myc function.

As described above, viral small-t antigen leads to stabilization of the c-Myc protein by protecting c-Myc serine 62 from PP2A-mediated dephosphorylation. In order to study if depletion of KIAA1524 regulates c-Myc expression, we examined c-Myc steady-state protein levels by western blotting from cells transfected with KIAA1524 or scrambled (Scr.) siRNA. KIAA1524 siRNA treatment resulted in clear downregulation of c-Myc protein expression, whereas c-Myc mRNA expression levels were not altered in the same samples (FIGS. 4A and 4B). This implies that KIAA1524 regulates c-Myc protein levels post-transcriptionally. Indeed, the analysis of the effect of KIAA1524 depletion on the half-life of endogenous c-Myc protein revealed that whereas in scrambled siRNA transfected cells approximately 40% of c-Myc protein was present in cells 1 h after cycloheximide treatment (100 mg/ml), KIAA1524 depletion significantly reduced c-Myc protein stability.

KIAA1524 Inhibits c-Myc-Associated PP2A Activity

The results above demonstrate that KIAA1524 interacts with the PP2A complex and promotes c-Myc stability. To study whether KIAA1524 indeed inhibits c-Myc-associated PP2A activity, c-Myc immunoprecipitates from scrambled and KIAA1524 siRNA transfected cells were subjected to an in vitro PP2A assay using 6,8-difluoro-4-methylumbelliferyl phosphate as the substrate (Pastula et al., 2003) Importantly, KIAA1524 depletion by siRNA markedly increased PP2A activity in c-Myc immunoprecipitates (FIG. 4C). Interestingly, analysis of immunoprecipitates further revealed that PP2Ac and c-Myc are constitutively in complex with each other and that depletion of KIAA1524 has no effect on c-Myc-PP2Ac interaction (FIG. 4D). Together, these results demonstrate that KIAA1524 inhibits PP2A activity in the c-Myc-PP2A complex and prevents proteolytic degradation of c-Myc.

Figure 5A:
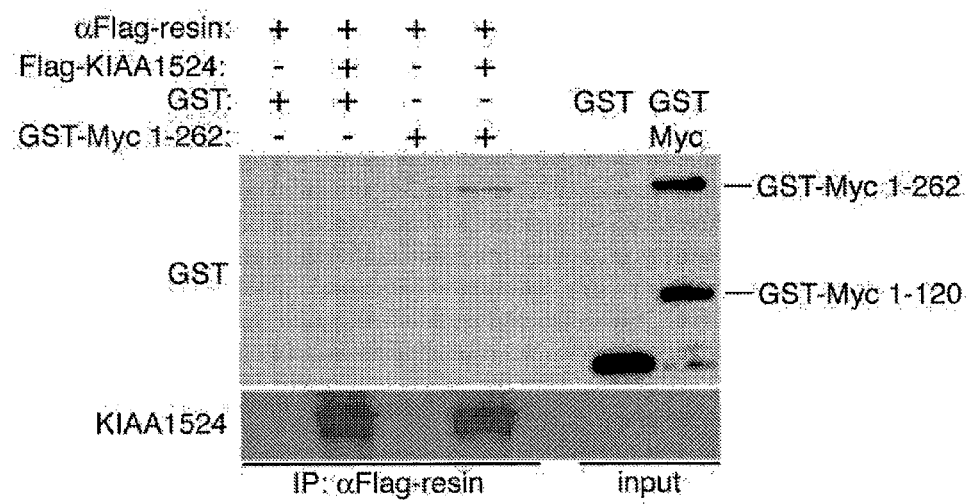
FIG. 5A) In vitro binding assay with immobilized, recombinant Flag-KIAA1524 protein and recombinant GST protein or with GST-c-Myc 1-262 protein. Immunoblots of eluates with GST (top) or KIAA1524 (bottom). Input, GST proteins used for interaction assay. Shown is a representative blot of three independent experiments with similar results.
Figure 5B:
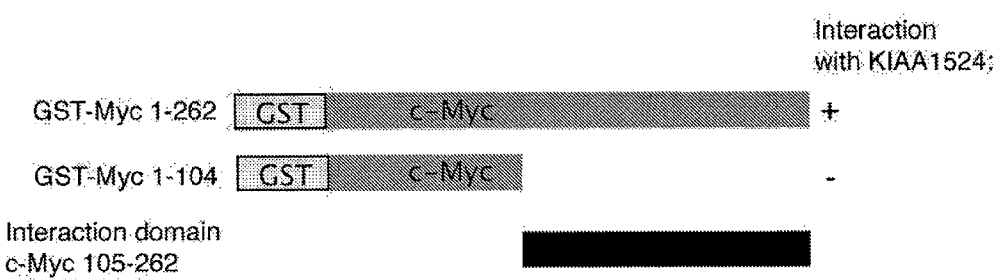
FIG. 5B) Schematic presentation of identification of c-Myc 105-262 as KIAA1524 binding domain on c-Myc. KIAA1524.

Co-immunoprecipitation of c-Myc and KIAA1524 from cellular extracts demonstrates a physical association between these proteins (FIG. 4D), but does not reveal whether the interaction between KIAA1524 and c-Myc is direct. To further characterize KIAA1524's interaction with c-Myc, purified Flag-KIAA1524 protein was used in an in vitro protein-protein interaction assay with recombinant GST-fused aminoterminal portion of c-Myc (aa. 1-262). We found that Flag-antibody resin co-immunoprecipitated recombinant Flag-KIAA1524 and GST-Myc, whereas Flag-KIAA1524 did not co-immunoprecipitate with GST alone (FIG. 5A), demonstrating that KIAA1524 directly binds to the c-Myc aminoterminus. Interestingly, KIAA1524 did not co-immunoprecipitate with GST-c-Myc deletion corresponding to aminoacids 1-120 (FIG. 5A). These results indicate that KIAA1524 interaction domain in c-Myc is between aminoacids 120-262 on c-Myc (FIG. 5B).

Together these experiments provide solid biochemical evidence that KIAA1524 inhibits c-Myc-associated PP2A activity. Moreover, direct binding of KIAA1524 to c-Myc aminoterminus provides the most feasible explanation for the observed selectivity of KIAA1524 towards c-Myc-associated PP2A activity.

KIAA1524 is Required for Tumor Growth

Figure 6A:
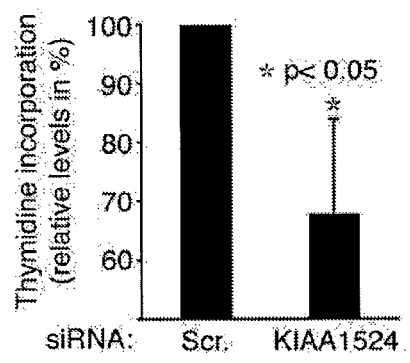
FIG. 6(A) Thymidine incorporation of HeLa cells transfected for 72 h with scrambled or KIAA1524 siRNA for cell proliferation. Shown is mean±S.D. of four experiments. * $p<0.05$, Student's t-test.
Figure 6B:
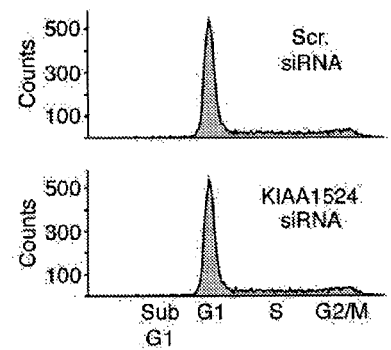
FIG. 6B) Flow cytometric analysis of DNA content for cell cycle progression from HeLa cells transfected with scrambled or KIAA1524 siRNA for 72 h. Results are from a representative experiment of four repetitions with similar results.
Figure 6C:
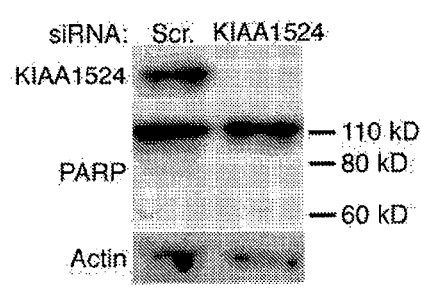
FIG. 6C) KIAA1524 depletion does not induce Poly (ADP-ribose) Polymerase (PARP) cleavage in HeLa cells as detected by immunoblotting 72 h after KIAA1524 siRNA transfection. Expected molecular weights of the full-length (110 kD) and caspase-cleaved forms of PARP proteins are shown on the right.

In order to study the role of KIAA1524 in regulation of cancer cell behavior, we transfected HeLa cells with KIAA1524 siRNA and studied cell proliferation in both cell culture and in in vivo mouse model. The role of KIAA1524 in regulating cell proliferation was next analyzed by thymidine incorporation assay in HeLa cells. Compared to scrambled siRNA transfected cells, KIAA1524 depletion resulted in significant inhibition of cell proliferation 72 h after transfection (FIG. 6A). However, KIAA1524 siRNA transfection did not induce a sub-G1 fraction in FACS analysis of the cellular DNA content (FIG. 6B), nor did it induce cleavage of the PARP protein (FIG. 6C), demonstrating that KIAA1524 depletion does not induce programmed cell death.

Figure 6D:
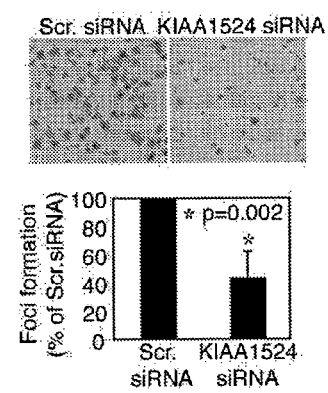
FIG. 6D) Dense foci formation on a monolayer of HeLa cells transfected with scrambled or KIAA1524 siRNA. Above, representative light miscroscopy images. Below, quantitation of number of foci 10 days after re-plating by Image J software. Shown is average+S.D. of four experiments. * $p=0.002$, Student's t-test.
Figure 6:
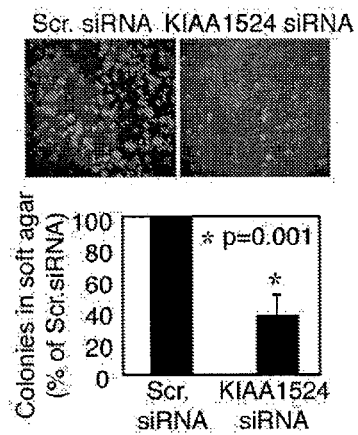
FIG. 6. KIAA1524 is required for cancer cell growth.

To assess the contribution of KIAA1524 on the tumorigenic potential of HeLa cells, the effects of KIAA1524 depletion on the ability of these cells to form dense foci on a monolayer, as well as their ability to grow in an anchorage-independent manner was analyzed. For this purpose, we first studied the efficiency of KIAA1524 depletion by a single transfection of siRNA 10 days after transfection and found that approximately 50% of KIAA1524 protein expression was still reduced after 10 days. KIAA1524 depletion abrogated HeLa cell foci formation 10 days after transfection (FIG. 6D) and also. clearly inhibited HeLa cell anchorage independent growth on agar as measured 10 days after plating of the cells on agar (FIG. 6E).

Figure 6F:
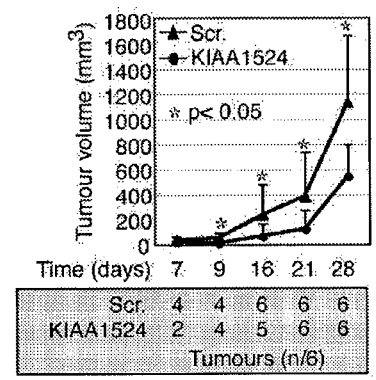
FIG. 6F) HeLa cells transfected with scrambled (Scr) or KIAA1524 siRNA were analyzed for tumor growth in immunocompromised mouse. Shown is mean±SD of tumor volumes from six mice in each group.
Figure 6G:
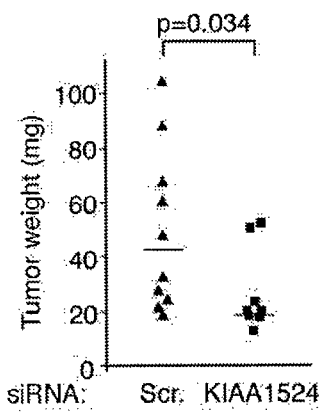
FIG. 6G) Weights (mg) of tumors from an independent experiment performed similarly to the experiment shown in FIG. 6F) at day 27. * $p=0.034$, Mann-Whitney U test.

To assess the tumorigenic role of KIAA1524 in vivo, HeLa cells transfected with either KIAA1524 or scrambled siRNA for 72 h were subcutaneously injected into athymic mice and tumor growth was monitored by measuring the size of palpable tumors. Importantly, depletion of KIAA1524 by siRNA reduced the overall tumor size (FIG. 6F), and resulted in a significant inhibition of tumor weight at day 27 (FIG. 6G).

Taken together, these data demonstrate that KIAA1524 expression is a novel mechanism of maintenance for the transformed cellular phenotype and that KIAA1524 promotes in vivo tumor growth.

KIAA1524 is Overexpressed in Human Malignancies

Figure 7A:
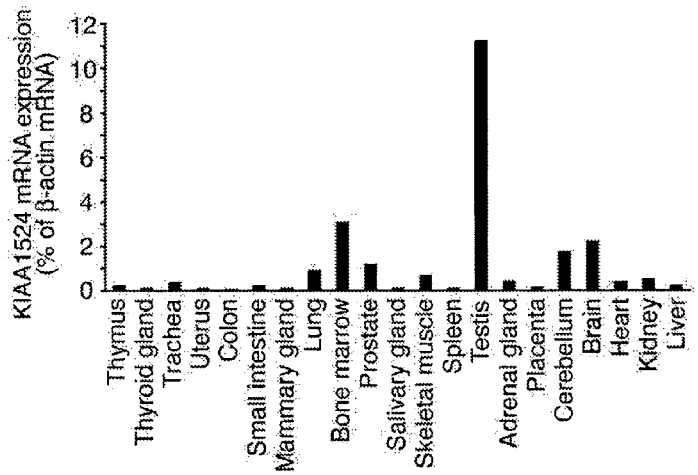
FIG. 7A) KIAA1524 mRNA mRNA expression was quantitated by quantitative RT-PCR analysis from normal tissue samples. KIAA1524 expression is presented relative to β-actin.

Results presented above provide evidence that KIAA1524 inhibits PP2A-mediated c-Myc degradation and promotes cancer cell growth and proliferation. Based on these characteristics, KIAA1524 could be a novel drug target for cancer therapeutics. In order to fulfill the expectations for a protein targeted in cancer therapies, KIAA1524 should preferably be overexpressed in human cancer tissues. According to our quantitative RT-PCR analysis, KIAA1524 mRNA was expressed at very low levels (<1% of βactin mRNA expression levels) in the majority of the 21 non-malignant samples, with the exception of bone marrow, prostate, testis, cerebellum and brain (FIG. 7A). To compare the protein levels of KIAA1524 between non-malignant and malignant cells, whole cell lysates of different cell types were immunoblotted for KIAA1524. Consistent with FIG. 7A, very low levels of KIAA1524 protein was detected in human epidermal keratinocytes (HEK), non-tumorigenic MEFs and immortalized NIH3T3 mouse fibroblasts. However, KIAA1524 protein was expressed at high levels in both HeLa cells and in HT-1080 fibrosarcoma cells, indicating that KIAA1524 expression may correlate with the tumorigenic potential of cells.

Figure 7B:
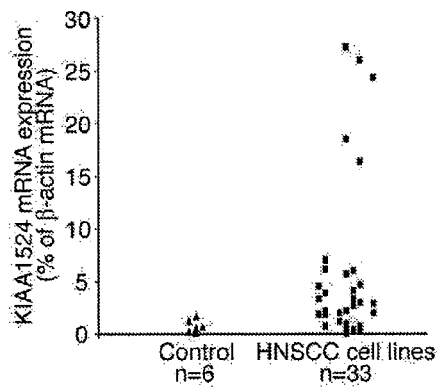
FIG. 7B) KIAA1524 mRNA expression was studied from HNSCC cell lines and from human epidermal keratinocytes (HEK) by Taqman real-time PCR analysis.
Figure 7C:
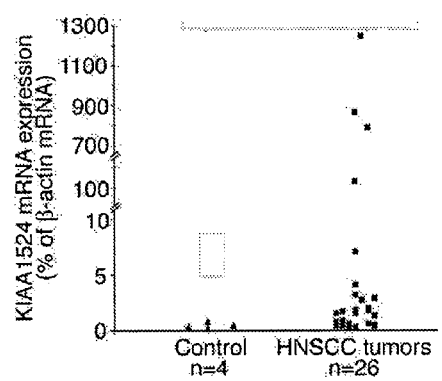
FIG. 7C) KIAA1524 mRNA expression was studied from HNSCC tumor samples and from normal tissue control samples by Taqman real-time PCR analysis.
Figure 7D:
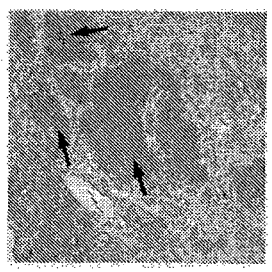
FIG. 7D) Immunostaining analysis of HNSCC tissue with KIAA1524 antibody shows intense cytoplasmic KIAA1524 staining in tumor cells (tumor cell nodules indicated by arrows).

Furthermore, KIAA1524 expression levels in human squamous cell carcinomas of the head and neck (HNSCC) were analyzed. Real-time PCR analysis of KIAA1524 mRNA showed statistically significant overexpression of KIAA1524 in 36 HNSCC cell lines as compared to normal human epidermal keratinocytes used as a control (FIG. 7B). KIAA1524 mRNA was also overexpressed in HNSCC tumor biopsies as compared to benign control tissues from the same region of the body (FIG. 7C). Importantly, immunohistochemical staining of HNSCC samples also confirmed higher expression of KIAA1524 in tumor cells as compared to surrounding stromal cells (FIG. 7D).

Figure 7E:
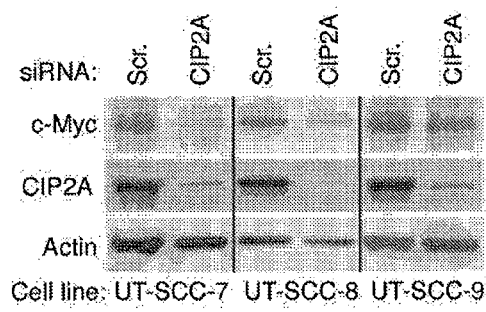
FIG. 7E) siRNA-induced depletion of KIAA1524 protein results in downregulation of c-Myc protein expression in HNSCC cell lines.

Finally, in order to study if KIAA1524 regulates c-Myc protein levels also in primary cancer cell lines derived from HNSCCs, three different HNSCC cell lines were transfected with KIAA1524 siRNA and analyzed for c-Myc expression by western blotting. As shown in FIG. 7E, KIAA1524 depletion resulted in clear downregulation of c-Myc protein levels in all cell lines examined. Importantly, analysis of c-Myc immunoprecipitates revealed that KIAA1524 depletion also increased c-Myc associated PP2A phosphatase activity in HNSCC cell lines.

To examine the role of KIAA1524 in the regulation of HNSCC cell proliferation, UT-SCC-7 and UT-SCC-9 cell lines were subjected to KIAA1524 siRNA transfection and dense foci formation of these cell lines was monitored for 10 days. In both cell lines, depletion of KIAA1524 resulted in a significant reduction in foci formation. Importantly, KIAA1524 depletion also significantly reduced anchorage independent growth of both UT-SCC-7 and UT-SCC-9 cells in soft agar 21 days after transfection. Consistent with the demonstrated specificity of KIAA1524 siRNAs in HeLa cells, two independent KIAA1524 siRNAs yielded a similar inhibition in soft agar growth of UT-SCC-9 cells.

Finally, to assess the role of KIAA1524 for in vivo tumor growth of UT-SCC cells, both UT-SCC-7 and UT-SCC-9 cells transfected with KIAA1524 or scrambled siRNAs were injected into the back of SCID mice. Consistent with all the other data presented in this work indicating the importance of KIAA1524 for malignant cell growth and tumor progression, only 3 out of 5 and 2 out of 6 mice injected with KIAA1524 siRNA transfected UT-SCC-7 and UT-SCC-9 cells, respectively, developed palpable tumors at day 65 when the experiment was terminated. Moreover, KIAA1524 siRNA reduced the average size of tumors with both of the UT-SCC cells, as compared to scrambled siRNA transfected cells.

Figure 8A:
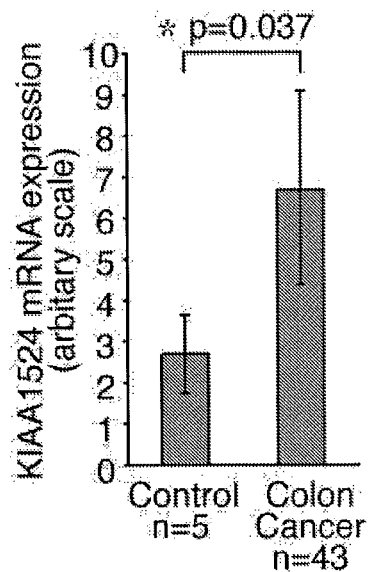
FIG. 8A) Quantitative RT-PCR analysis of KIAA1524 mRNA expression in colon cancer tissues and in non-malignant colon tissues (control). Shown is mean expression of samples+S.D. * $p<0.05$, Mann-Whitney U test.

To confirm that the above results are restricted to HNSCC, KIAA1524 expression was analyzed from 43 human colon cancer samples and 5 control samples from normal colon by RT-PCR. In accordance with the HNSCC data, KIAA1524 mRNA was significantly overexpressed in human colon cancer tissues as compared to control tissues (FIG. 8A).

Figure 8B:
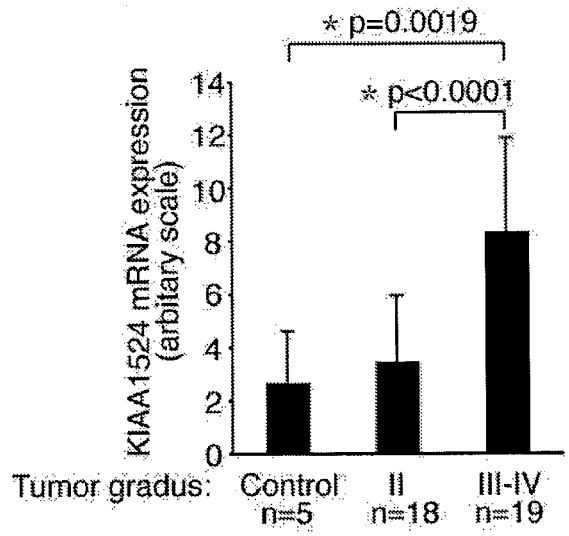
FIG. 8B) Association between KIAA1524 expression level and tumor gradus in human colon cancers. Statistical difference in KIAA1524 expression between gradus III-IV and gradus II (* $p<0.0001$, Mann-Whitney U test) and between gradus III-IV and normal samples (* $p=0.0019$, Mann-Whitney U test) was observed.

Furthermore, comparison of KIAA1524 mRNA expression to colon cancer tumor gradus revealed that KIAA1524 expression is significantly higher in invasive gradus III and gradus IV tumors as compared to non-invasive gradus II tumors or control colon tissue (FIG. 8B). The tumor gradus of the tissue samples used for the analysis have previously been determined by standard pathological criteria.

Figure 9A:
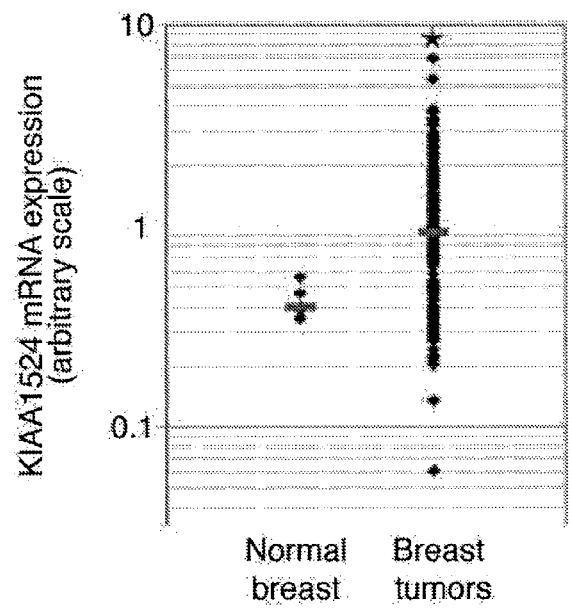
FIG. 9A) KIAA1524 expression in normal or tumoral mammary tissue.
Figure 9B:
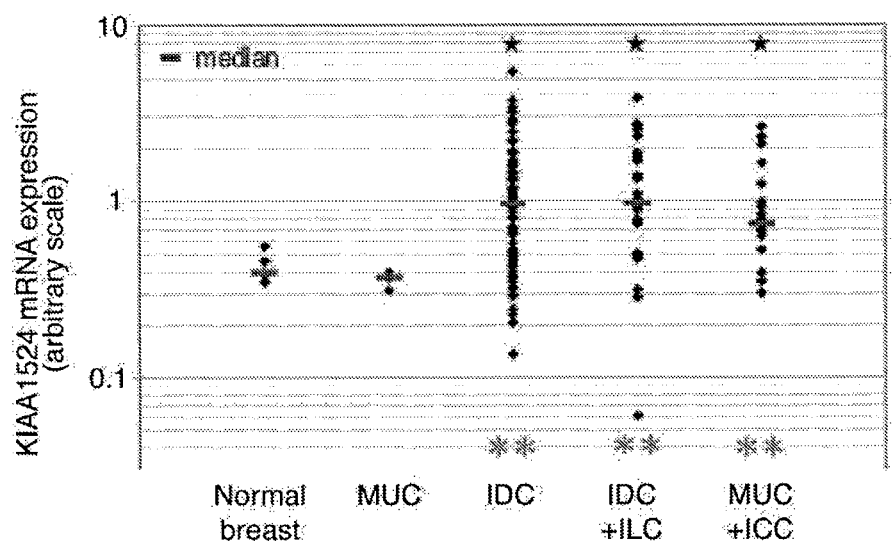
FIG. 9B) KIAA1524 expression depends on human mammary tumor type. Two-sample Wilcoxon (Mann-Whitney) rank-sum test was used for statistical analysis. *: $p<0.05$ compared to normal breast; ** $p<0.005$ compared to mucinous tumors. House-keeping gene β-actin was used for normalization.

In order to study if KIAA1524 is over-expressed, in addition to HNSCC and colon cancer, also in breast cancer samples, KIAA1524 expression was evaluated in 159 previously characterized human mammary tumors and normal breast samples (Come et al., 2006). Importantly, it was found that KIAA1524 is significantly over-expressed in human mammary tumors when compared to normal tissue (FIG. 9A). When comparing KIAA1524 expression between breast cancer sub-types, over-expression of KIAA1524 was found in all three invasive mammary cancer sub-types, invasive ductal carcinoma (IDC), invasive lobular carcinoma (ILC) and IDC with intraductal comedo carcinoma (IDC+ICC) (FIG. 9B). As a control, mucinous carcinomas, that are mammary tumors with good prognosis, presented similar KIAA1524 mRNA expression than normal breast, statistically lower than invasive tumors (FIG. 9B).

Taken together, results of this demonstrate that KIAA1524 promotes tumor growth and cancer cell proliferation and strongly indicate that suppression of c-Myc associated PP2A activity is at least one of the molecular mechanisms by which KIAA1524 exerts its cellular effects.

Materials and Methods

Antibodies

Rabbit polyclonal antibody for KIAA1524 has been published (Soo Hoo et al., 2002) (generously provided by Dr. Chan, University of Florida). Antibodies for PP2Ac, PR65, Flag, HA, GST, PARP, c-Myc and Actin were obtained from Santa Cruz biotechnologies inc.

Plasmid Constructs

PR65TAP-tag vectors PR65α was PCR amplified from pRC/CMV.HA PR65a (a kind gift from Dr. Brian A. Hemmings, Friedrich Miescher-Institut, Basel, Switzerland),) and cloned into the TAP vector, JW16 (Westermarck et al., 2002), using XhoI and BamHI sites. Flag-KIAA1524 wt constructs was constructed with PCR from published KIAA1524 full-length cDNA (Soo Hoo et al., 2002) (generously provided by Dr. Chan, University of Florida). Flag-KIAA1524mut cDNA construct was constructed with PCR from plasmid Flag-KIAA1524 wt with PCR using oligos: 5-Ttaatagagaaact-tcagtctggaatg (SEQ ID NO. 80) and 5-Gtggtaaaggatcagatttgt-gatgtgaga (SEQ ID NO. 81). All clones were thereafter verified by DNA sequencing.

Patient Samples

After informed consent, tumor samples were collected from surgically removed tumors from HNSCC between years 1990-2002 in Turku University Central Hospital. Normal samples were collected from patients undergoing uvulo-palato-pharyngoplasty for a HNSCC study. Samples were collected from both genders ranging in age from 29-87 years old.

Expression of KIAA1524 in colon cancer and normal colon tissue was examined by using TissueScan Real-Time Colon Cancer (HCRT101) cDNA panel (Origene), containing 43 samples from colon cancer (both genders ranging in age from 31-93 years) and 5 samples of normal colon tissues (both genders ranging in age from 37-91 years). Total RNA extracted from 21 different normal human tissues was obtained from BD Biosciences (Palo Alto, Calif.) and was a generous gift from Prof. Klaus Elenius, University of Turku, Finland. Samples consisted either of RNA extractions from single patients (cerebellum, brain, heart, liver, and lung) or of pooled RNA extractions from 2 to 84 patients (adrenal gland, bone marrow, kidney, placenta, prostate, salivary gland, skeletal muscle, spleen, thymus, thyroid gland, trachea, uterus, colon, small intestine, and mammary gland).

Expression of KIAA1524 in breast cancer and normal mammary tissue was examined by using previously described tissue samples (Come et al., 2006).

Cell Cultures

Human SCC cell lines were established from primary tumors (UT-SCC-8), recurrent tumors, or metastasis (UT-SCC-7, UT-SCC-9) of head and neck SCCs. SCC cells were cultured in DMEM supplemented with 6 nmol/l glutamine, nonessential amino acids, 100 U/ml penicillin, 100 mg streptomycin, and 10% fetal calf serum (FCS). Normal human epidermal keratinocytes were cultured in Keratinocyte Basal Medium 2 (KBM®-2) supplemented with SingleQuots® (Cambrex Bioscience; Walkersville, Md., USA). All other cells lines, including HT-1080, HeLa and HK293 were cultured in DMEM supplemented with 100 U/ml penicillin, 100 mg streptomycin, and 10% FCS.

Transient Transfections and siRNA Treatment

Subconfluent cells were transiently transfected using FuGene 6 Transfection reagent (Roche) according to the manufacturer's instructions. For siRNA treatments, cells were grown to 80% confluence and medium was replaced with DMEM without supplements. Double-stranded RNA oligonucleotides (scrambled: 5'-UAACAAUGAGAG-CACGGCTT-3' (SEQ ID NO. 82) and 5'-CCUACAUC-CCGAUCGAUGAUGTT-3' (SEQ ID NO 83); KIAA1524: 5'-CUGUGGUUGUGUUUGCACUTT-3' (SEQ ID NO. 84) and 5'-ACCAUUGAUAUCCUUAGAATT-3' (SEQ ID NO 6); IBA) were prepared with Oligofectamine™ reagent (Invitrogen) and added to the cells. After 4-6 h incubation, the medium was equilibrated to 10% FCS and the siRNA treatment was extended for the appropriate length of time.

RNA Isolation and cDNA Synthesis

Total RNA was extracted from cultured cells using TRIzol reagent (Invitrogen) according to the manufacturer's protocol. From clinical tumor samples, RNA was extracted using acid-guanidium thiocyanate-phenol-chloroform method. To eliminate possible contaminating DNA, RNA samples were treated with 5 units of DNase I (Roche). cDNA was synthesized in a reaction containing 1 μg of total RNA as a template, 0.5 μg random hexamers and 200 units of Moloney murine leukemia virus RNase H minus reverse transcriptase (both from Promega; Madison, Wis., USA), in a total volume of 25 μl according to the manufacturer's protocol.

Immunofluorescence 24 hours after transfection with HA-PP2Ac and Flag-KIAA1524 cDNA constructs, HeLa cells cultured on glass coverslips were permeabilized and fixed for 10 minutes in PTEMF (100 mM Pipes (pH 6.8), 10 mM EGTA, 1 mM MgCl2, 0.2% Triton X-100, and 4% formaldehyde). After three washes with PBS nonspecific antibody binding was blocked for 30 minutes with 3% BSA in PBS. Coverslips were thereafter incubated with HA and Flag-tag specific antibodies for 1 h in RT in 2% BSA in PBS. After three washes, bound antibodies were visualized by incubation with Cy3 and Cy2 and -conjugated secondary antibody (Jackson ImmunoResearch) for 1 hour at room temperature. After three washes with PBS, the coverslips were mounted in 50% glycerol, PBS, and 2% w/v DABCO (Sigma-Aldrich). For analysis of co-localization, images were acquired using a confocal laser scanning microscope (LSM 510, Carl Zeiss Inc.).

Immunoprecipitations and Phosphatase Assays

Protein G-Sepharose beads were agitated on a tumbler for 2 h at 4 C with PR65, PP2Ac, c-Myc antibodies or with control pre-immune serum in 20 mM HEPES-KOH pH 7.5, 300 mM NaCl, 0.25 mM EGTA, 1.5 mM MgCl2, 0.25% NP-40, protease inhibitors (Roche), 10 mM b-glyserolphos-phate and 0.5 mM DTT. Immunoprecipitation of Flag-KIAA1524 mutants was performed by using Flag-antibody resin (M3, Sigma). Thereafter, sedimented beads were mixed with cellular lysates and incubated for over-night in 4 C. Thereafter the sedimented beads were washed four times with 50 mM Tris-HCl pH 7.4, 150 mM NaCl, 0.3% NP-40 and 0.5 mM DTT, and bound proteins were analyzed by western blotting using True-blot secondary antibodies. For phsophatase assays, immunocomplexes were retained on beads and equal amounts of beads were added to phosphatase assays using the Protein Serine/Threonine Phosphatase Assay kit with 6,8-difluoro-4-methylumbelliferyl phosphate (DiFMUP) substrate (Molecular Probes, Eugene, Oreg. USA) according to the manufacturer's instructions.

To study direct interaction between KIAA1524 and c-Myc, Flag-KIAA1524 was baculovirally expressed in insect cells and affinity purified to homogeneity by Flag-antibody resin (M3, Sigma), as described previously (Nordlund et al., 2005). For interaction assays Flag-KIAA1524 protein was eluated from Flag-Ab beads by using low Ph conditions. The purity and quantity of this KIAA1524 protein was analyzed in each step by SDS-page gel and coomassie staining. No other contaminating proteins were identified in the KIAA1524 preparates. GST protein was bacterially produced and affinity purified according standard protocols and GST-Myc1-262 was purchased from Santa Cruz Inc. Pull-down assay was performed by incubating 1 μg of Flag-KIAA1524 immobilized on anti-Flag M3 resin (Sigma) with molar equivalent amounts of soluble GST-c-Myc and GST proteins in 0.5 ml of buffer containing 20 mM Tris (pH 7.4), 0.2 mM EDTA, 0.1 M NaCl, 0.5 mM DTT and Complete protease inhibitors (Roche). Absence of insect PP2A in KIAA1524 protein preparate was controlled by phosphatase assay. Anti-Flag M3 resin was used as a control resin in all experiments. Bound proteins were washed in binding buffer supplemented with 0.2% NP-40 and subsequently boiled in sample buffer, resolved in SDS-PAGE and immunoblotted with GST and KIAA1524 antibodies.

Quantitative Reverse Transcription-PCR Analysis

Quantitative real-time reverse transcription-PCR (RT-PCR) analysis of cDNA samples was performed with specific primers and fluorescent probes designed using Primer Express software (PE Biosystems) to specifically quantitate the levels of KIAA1524 and β-actin mRNA. The sequences of the primers and probes are shown below:

```
KIAA1524:
Probe:
                              (SEQ ID NO. 85)
att gct cag cat cgc tgt caa aga act ca Forward:
                              SEQ ID NO. 86)
aag ctc tag ccc ttg cac agg Reverse:
                              (SEQ ID NO. 87)
gtc cgt gcc tct gtt tca gc β-actin:
Probe:
                              (SEQ ID NO. 88)
atg ccc tcc ccc atg cca tcc tgc gt Forward:
                              (SEQ ID NO. 89)
tca ccc aca ctg tgc cca tct acg c Reverse:
                              (SEQ ID NO. 90)
cag cgg aac cgc tca ttg cca atg g
```

PCR was carried out in a solution containing 300 nM of primers (Medprobe), 200 nM of 5' 6-FAM (PE Biosystems), 12.5 μl of TaqMan universal PCR Master Mix (PE Biosystems), and 0.5 μl of template cDNA in a final volume of 25 μl. Thermal cycling was performed with ABI PRISM 7700 Sequence Detector (PE Biosystems). Cycling was initiated with 2 min at 50° C. and 10 min at 95° C., followed by 40 cycles of 15 s at 95° C. and 1 min at 60° C. Accumulation of the specific PCR products was detected real-time as an increase in fluorescence. Observed fluorescence was plotted against cycle number to generate amplification plots and to determine CT values, i.e. the cycle numbers at which the fluorescence signal exceeded a CT value of 0.05 relative fluorescence units. Each determination of a CT value was done in duplicate and normalized with the CT values of simultaneous duplicate measurements of β-actin expression from the same samples. The range between two parallel CT values was <5% of the mean in all of the measurements. Relative expression of the gene analyzed (target gene) was estimated using the formula: relative expression=$2-\Delta CT$, where $\Delta CT=CT(\text{target gene})-CT(\beta\text{-actin})$. The quantity of mRNAs was expressed as percentage of the quantity of β-actin mRNA after multiplying relative target gene expression by a factor of 100.

Soft Agar Growth, Foci Formation and Tumor Formation in Mouse

For foci formation assay and anchorage-independent growth in soft agar, HeLa-cells were trypsinated and seeded to $4 \times 10^5$ cells at 10 cm plates 48 hours after siRNA treatment. Soft-agar assays were performed in medium containing 10% FBS as described in the literature. After 9 days incubation cultures were photographed double-blindly. The numbers of viable colony formatting cells were measured from microscopy images (×5 magnification). The number and size of colonies from each image of view were analyzed using ImageJ 1.33u software from NIH (http://rsb.info.nih.gov/ij/). Anchorage independent colonies were classified according to number between 200-10,000 pixels.

For foci formation assays in MEFs, 200 or 500 cells of the retrovirally transduced MEFs were plated with $8.3 \times 10^5$ NIH3T3 cells as feeders per well in a 6 well plate. Cells were grown for 1-2 weeks. Methanol-fixed cells were stained with Giemsa. Foci numbers were calculated per 100 infected cells.

For the mouse experiments, $3 \times 10^6$ transfected cells were injected subcutaneously to the flank of immunocompromised mouse. Tumor formation was evaluated thereafter every third day by palpation, and the size of the palpable tumors was measured by precision instrument. The experiment was terminated at the day 28. All experiments with mice were performed according to institutional animal care guidelines and with the permission of the animal test review board of the University of Turku, Finland.

Western Blot Analysis

Following protein separation by SDS-PAGE gel electrophoresis the proteins were transferred to Immobilo-P membrane (Millipore; Billerica, Mass., USA). After incubation with primary and secondary antibodies, immunoblotted proteins were visualized by enhanced chemiluminescence (ECL; Amersham Biosciences).

Immunohistochemistry

Immunostaining of paraffin-embedded tumor sections and control tissue sections for KIAA1524 was performed using 1:100 dilution of p90 antibody (Soo Hoo, et al., 2002) in PBS. Immunostaining was done with avidin-biotin-peroxidase complex technique (VectaStain; Vector Labs; Burlingame, Calif., USA) in combination with diaminobenzidine (DAB), and counterstained with hematoxylin.

Preparation of Lysates for Tandem Affinity Purification

HT-1080 cells stably expressing PR65TAP protein were washed with phosphate buffered saline (PBS) and resuspended in Buffer A (10 mM Hepes pH 7.9, 10 mM KCl, 0.1 mM EDTA, 0.1 mM EGTA, 1.5 mM MgCl2, Complete Protease Inhibitor, 20 mM b-glycerolphosphate, 25 mM NaF, 0.5 mM PMSF, and 0.5 mM DTT). Cells were incubated on ice, vortexed and then centrifuged at 3900 rpm for 3 min to obtain the cytoplasmic lysate. Extracts were then adjusted to contain similar levels of NaCl and NP-40 as IgG Binding Buffer (IBB; 10 mM Tris HCl pH 8.0, 150 mM NaCl, 0.2% NP-40, 0.5 mM DTT). Adjusted extracts were then loaded onto Poly-Prep® chromatography columns (BioRad) containing IgG sepharose 4 Fast Flow (Amersham) washed with IBB. Extracts were incubated for 4 h at 4° C. followed by 3×10 ml washes of IBB. The beads were then incubated in TEV cleavage buffer (TCB; 10 mM Tris HCl pH 8.0, 150 mM NaCl, 0.3% NP-40, 0.5 mM EDTA, and 0.5 mM DTT) and recombinant tobacco etch virus protease (TEV) overnight at 4° C. Calmodulin beads (Startagene) are washed in Poly-Prep® chromatography columns with Calmodulin Binding Buffer (CBB; 10 mM b-mercaptoethanol, 50 mM Tris HCl pH 8.0, 150 mM NaCl, 1 mM Mg-acetate, 1 mM imidazole, 2 mM CaCl2, and 0.2% NP-40). The TEV eluate was then recovered from the column and adjusted for binding to calmodulin beads (4 ml of 1 M CaCl2 and 3 ml of CBB for every 1 ml of eluate). The adjusted eluate is incubated for 2 h at 4° C. and then washed 3×10 ml with CBB. The proteins bound to the calmodulin beads are then recovered either with Calmodulin Elution Buffer (CEB; 10 mM b-mercaptoethanol, 10 mM Tris HCl pH 8.0, 150 mM NaCl, 1 mM Mg-acetate, 1 mM imidazole, 5 mM EGTA, and 0.2% NP-40) or boiled in SDS loading buffer.

Mass Spectrometric Protein Identification

The protein bands of interest were excised from the gel, reduced, alkylated, and digested overnight with trypsin as described previously. Extracted peptides were characterized by LC-MS/MS on a hybrid linear ion-trap instrument (Q-Trap, Applied Biosystems, Framingham, Mass., USA), coupled to a nanoflow HPLC system (LC Packings, San Francisco, Calif., USA). The resulting peptide fragment spectra were searched against a comprehensive non-redundant protein database, using Mascot. A minimum of three matching tryptic peptides was required to identify each protein, and correct fragment ion assignment was guaranteed by manual inspection, if necessary.

Gene Expression Analysis

Total RNA extracted from HeLa cells 72 h after transfection with either scrambled or KIAA1524 siRNA was analysed for genome-wide gene expression profiles by Sentrix® Human-6 Expression BeadChip array (Illumina Inc.). cDNA amplification, labeling and hybridization were done according the manufacturers instruction and standard procedures at the Finnish DNA Microarray Centre (Centre for Biotechnology, University of Turku and Abo Akademi University, Turku, Finland). The data obtained from array was analyzed by Bioinformatics core facility personal at the Centre for Biotechnology, University of Turku and Abo Akademi University, Turku, Finland. The list 76 genes which expression was significantly altered in response to KIAA1524 depletion was filtered following criteria of at least log 0.5 change in the expression levels in both of the two experiments, as compared to scrambled siRNA transfected cells.

Statistical Methods

For FIGS. 6G, 8A, 8B, 9A and 9B the statistical significance was determined by Mann-Whitney U test and for all the other experiments displaying statistical analysis it was performed by Student's t-test.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

REFERENCES

Come, C., Magnino, F., Bibeau, F., De Santa Barbara, P., Becker, F. K., Theillet, C. and Savagner, P. (2006) *Clinical Cancer Research,* 12, 5395-5402.

Janssens, V. and Goris, J. (2001) Protein phosphatase 2A: a highly regulated family of serine/threonine phosphatases implicated in cell growth and signalling. *Biochem J,* 353, 417-439.

Kim D. H, Behlke M. A, Rose S. D, Chang M. S, Choi S and Rossi J. J. (2005) Synthetic dsRNA Dicer substrates enhance RNAi potency and efficacy. *Nat Biotechol,* 23, 222-226.

Nordlund, H. R., Laitinen, O. H., Uotila, S. T., Kulmala, M., Kalkkinen, N., and Kulomaa, M. S. (2005). Production of Hey b5 as a fluorescent biotin-binding tripartite fusion protein in insect cells. *Biochem Biophys Res Commun* 336, 232-238.

Pastula, C., Johnson, I., Beechem, J. M., and Patton, W. F. (2003). Development of fluorescence-based selective assays for serine/threonine and tyrosine phosphatases. *Comb Chem High Throughput Screen* 6, 341-346.

Soo Hoo, L., Zhang, J. Y. and Chan, E. K. (2002) Cloning and characterization of a novel 90 kDa 'companion' auto-antigen of p62 overexpressed in cancer. *Oncogene,* 21, 5006-5015.

Westermarck, J., Weiss, C., Saffrich, R., Kast, J., Musti, A. M., Wessely, M., Ansorge, W., Seraphin, B., Wilm, M., Valdez, B. C. and Bohmann, D. (2002) The DEXD/H-box RNA helicase RHII/Gu is a co-factor for c-Jun-activated transcription. *EMBO J,* 21, 451-460.

Yeh, E., Cunningham, M., Arnold, H., Chasse, D., Monteith, T., Ivaldi, G., Hahn, W. C., Stukenberg, P. T., Shenolikar, S., Uchida, T., Counter, C. M., Nevins, J. R., Means, A. R. and Sears, R. (2004) A signalling pathway controlling c-Myc degradation that impacts oncogenic transformation of human cells. *Nat Cell Biol,* 6, 308-318.

Zhao, J. J., Roberts, T. M. and Hahn, W. C. (2004) Functional genetics and experimental models of human cancer. *Trends Mol Med,* 10, 344-350.

The invention claimed is:

1. Small interfering RNA comprising a nucleotide sequence selected from the group consisting of SEQ ID NO:s 2 to 6, and inhibiting KIAA1524.

2. A pharmaceutical composition comprising a small interfering RNA according to claim 1.

3. A method of inhibiting KIAA1524 in a human or animal patient in need thereof by administering a therapeutically effective amount of a pharmaceutical composition according to claim 2;

wherein said patient suffers from cancer.

4. The method according to claim 3, wherein said cancer is selected from the group consisting of squamous cell cancer of the head-and-neck region, breast cancer and colon cancer.

* * * * *

SEQUENCE LISTING

<160> NUMBER OF SEQ ID NOS: 90

<210> SEQ ID NO 1
<211> LENGTH: 905
<212> TYPE: PRT
<213> ORGANISM: Homo sapiens

<400> SEQUENCE: 1

Met Asp Ser Thr Ala Cys Leu Lys Ser Leu Leu Leu Thr Val Ser Gln
1               5                   10                  15

Tyr Lys Ala Val Lys Ser Glu Ala Asn Ala Thr Gln Leu Leu Arg His
            20                  25                  30

```
Leu Glu Val Ile Ser Gly Gln Lys Leu Thr Arg Leu Phe Thr Ser Asn
         35                  40                  45

Gln Ile Leu Thr Ser Glu Cys Leu Ser Cys Leu Val Glu Leu Leu Glu
 50                  55                  60

Asp Pro Asn Ile Ser Ala Ser Leu Ile Leu Ser Ile Ile Gly Leu Leu
 65                  70                  75                  80

Ser Gln Leu Ala Val Asp Ile Glu Thr Arg Asp Cys Leu Gln Asn Thr
                 85                  90                  95

Tyr Asn Leu Asn Ser Val Leu Ala Gly Val Val Cys Arg Ser Ser His
                100                 105                 110

Thr Asp Ser Val Phe Leu Gln Cys Ile Gln Leu Leu Gln Lys Leu Thr
                115                 120                 125

Tyr Asn Val Lys Ile Phe Tyr Ser Gly Ala Asn Ile Asp Glu Leu Ile
         130                 135                 140

Thr Phe Leu Ile Asp His Ile Gln Ser Ser Glu Asp Glu Leu Lys Met
145                 150                 155                 160

Pro Cys Leu Gly Leu Leu Ala Asn Leu Cys Arg His Asn Leu Ser Val
                165                 170                 175

Gln Thr His Ile Lys Thr Leu Ser Asn Val Lys Ser Phe Tyr Arg Thr
                180                 185                 190

Leu Ile Thr Leu Leu Ala His Ser Ser Leu Thr Val Val Phe Ala
         195                 200                 205

Leu Ser Ile Leu Ser Ser Leu Thr Leu Asn Glu Glu Val Gly Glu Lys
         210                 215                 220

Leu Phe His Ala Arg Asn Ile His Gln Thr Phe Gln Leu Ile Phe Asn
225                 230                 235                 240

Ile Leu Ile Asn Gly Asp Gly Thr Leu Thr Arg Lys Tyr Ser Val Asp
                245                 250                 255

Leu Leu Met Asp Leu Leu Lys Asn Pro Lys Ile Ala Asp Tyr Leu Thr
                260                 265                 270

Arg Tyr Glu His Phe Ser Ser Cys Leu His Gln Val Leu Gly Leu Leu
         275                 280                 285

Asn Gly Lys Asp Pro Asp Ser Ser Lys Val Leu Glu Leu Leu Leu
         290                 295                 300

Ala Phe Cys Ser Val Thr Gln Leu Arg His Met Leu Thr Gln Met Met
305                 310                 315                 320

Phe Glu Gln Ser Pro Pro Gly Ser Ala Thr Leu Gly Ser His Thr Lys
                325                 330                 335

Cys Leu Glu Pro Thr Val Ala Leu Leu Arg Trp Leu Ser Gln Pro Leu
                340                 345                 350

Asp Gly Ser Glu Asn Cys Ser Val Leu Ala Leu Glu Leu Phe Lys Glu
                355                 360                 365

Ile Phe Glu Asp Val Ile Asp Ala Ala Asn Cys Ser Ser Ala Asp Arg
         370                 375                 380

Phe Val Thr Leu Leu Leu Pro Thr Ile Leu Asp Gln Leu Gln Phe Thr
385                 390                 395                 400

Glu Gln Asn Leu Asp Glu Ala Leu Thr Arg Lys Lys Cys Glu Arg Ile
                405                 410                 415

Ala Lys Ala Ile Glu Val Leu Leu Thr Leu Cys Gly Asp Asp Thr Leu
         420                 425                 430

Lys Met His Ile Ala Lys Ile Leu Thr Thr Val Lys Cys Thr Thr Leu
         435                 440                 445
```

```
Ile Glu Gln Gln Phe Thr Tyr Gly Lys Ile Asp Leu Gly Phe Gly Thr
450                 455                 460

Lys Val Ala Asp Ser Glu Leu Cys Lys Leu Ala Ala Asp Val Ile Leu
465                 470                 475                 480

Lys Thr Leu Asp Leu Ile Asn Lys Leu Lys Pro Leu Val Pro Gly Met
                485                 490                 495

Glu Val Ser Phe Tyr Lys Ile Leu Gln Asp Pro Arg Leu Ile Thr Pro
                500                 505                 510

Leu Ala Phe Ala Leu Thr Ser Asp Asn Arg Glu Gln Val Gln Ser Gly
                515                 520                 525

Leu Arg Ile Leu Leu Glu Ala Ala Pro Leu Pro Asp Phe Pro Ala Leu
530                 535                 540

Val Leu Gly Glu Ser Ile Ala Ala Asn Asn Ala Tyr Arg Gln Gln Glu
545                 550                 555                 560

Thr Glu His Ile Pro Arg Lys Met Pro Trp Gln Ser Ser Asn His Ser
                565                 570                 575

Phe Pro Thr Ser Ile Lys Cys Leu Thr Pro His Leu Lys Asp Gly Val
                580                 585                 590

Pro Gly Leu Asn Ile Glu Glu Leu Ile Glu Lys Leu Gln Ser Gly Met
                595                 600                 605

Val Val Lys Asp Gln Ile Cys Asp Val Arg Ile Ser Asp Ile Met Asp
610                 615                 620

Val Tyr Glu Met Lys Leu Ser Thr Leu Ala Ser Lys Glu Ser Arg Leu
625                 630                 635                 640

Gln Asp Leu Leu Glu Thr Lys Ala Leu Ala Leu Ala Gln Ala Asp Arg
                645                 650                 655

Leu Ile Ala Gln His Arg Cys Gln Arg Thr Gln Ala Glu Thr Glu Ala
                660                 665                 670

Arg Thr Leu Ala Ser Met Leu Arg Glu Val Glu Arg Lys Asn Glu Glu
                675                 680                 685

Leu Ser Val Leu Leu Lys Ala Gln Gln Val Glu Ser Glu Arg Ala Gln
690                 695                 700

Ser Asp Ile Glu His Leu Phe Gln His Asn Arg Lys Leu Glu Ser Val
705                 710                 715                 720

Ala Glu Glu His Glu Ile Leu Thr Lys Ser Tyr Met Glu Leu Leu Gln
                725                 730                 735

Arg Asn Glu Ser Thr Glu Lys Lys Asn Lys Asp Leu Gln Ile Thr Cys
                740                 745                 750

Asp Ser Leu Asn Lys Gln Ile Glu Thr Val Lys Lys Leu Asn Glu Ser
                755                 760                 765

Leu Lys Glu Gln Asn Glu Lys Ser Ile Ala Gln Leu Ile Glu Lys Glu
                770                 775                 780

Glu Gln Arg Lys Glu Val Gln Asn Gln Leu Val Asp Arg Glu His Lys
785                 790                 795                 800

Leu Ala Asn Leu His Gln Lys Thr Lys Val Gln Glu Glu Lys Ile Lys
                805                 810                 815

Thr Leu Gln Lys Glu Arg Glu Asp Lys Glu Thr Ile Asp Ile Leu
                820                 825                 830

Arg Lys Glu Leu Ser Arg Thr Glu Gln Ile Arg Lys Glu Leu Ser Ile
                835                 840                 845

Lys Ala Ser Ser Leu Glu Val Gln Lys Ala Gln Leu Glu Gly Arg Leu
850                 855                 860
```

```
Glu Glu Lys Glu Ser Leu Val Lys Leu Gln Gln Glu Glu Leu Asn Lys
865                 870                 875                 880

His Ser His Met Ile Ala Met Ile His Ser Leu Ser Gly Gly Lys Ile
                885                 890                 895

Asn Pro Glu Thr Val Asn Leu Ser Ile
                900                 905

<210> SEQ ID NO 2
<211> LENGTH: 24
<212> TYPE: DNA
<213> ORGANISM: Artificial Sequence
<220> FEATURE:
<223> OTHER INFORMATION: Synthetic siRNA strand

<400> SEQUENCE: 2
aacatcagtg cttcactgat cctt                                              24

<210> SEQ ID NO 3
<211> LENGTH: 23
<212> TYPE: DNA
<213> ORGANISM: Artificial Sequence
<220> FEATURE:
<223> OTHER INFORMATION: Synthetic siRNA strand

<400> SEQUENCE: 3
aactgtggtt gtgtttgcac ttt                                               23

<210> SEQ ID NO 4
<211> LENGTH: 21
<212> TYPE: DNA
<213> ORGANISM: Artificial Sequence
<220> FEATURE:
<223> OTHER INFORMATION: Synthetic siRNA strand

<400> SEQUENCE: 4
gguugcagau ucgaauuat t                                                  21

<210> SEQ ID NO 5
<211> LENGTH: 21
<212> TYPE: DNA
<213> ORGANISM: Artificial Sequence
<220> FEATURE:
<223> OTHER INFORMATION: Synthetic siRNA strand

<400> SEQUENCE: 5
aaugccuugu cuaggauuat t                                                 21

<210> SEQ ID NO 6
<211> LENGTH: 21
<212> TYPE: DNA
<213> ORGANISM: Artificial Sequence
<220> FEATURE:
<223> OTHER INFORMATION: Synthetic siRNA strand

<400> SEQUENCE: 6
accauugaua uccuuagaat t                                                 21

<210> SEQ ID NO 7
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 7

Gly Phe Gly
1

<210> SEQ ID NO 8
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 8

Thr Lys Val
1

<210> SEQ ID NO 9
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 9

Ala Asp Ser
1

<210> SEQ ID NO 10
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 10

Glu Leu Cys
1

<210> SEQ ID NO 11
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 11

Lys Leu Ala
1

<210> SEQ ID NO 12
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 12

Ala Asp Val
1

<210> SEQ ID NO 13
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 13

Ile Leu Lys
1

<210> SEQ ID NO 14
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 14

Thr Leu Asp
1

<210> SEQ ID NO 15
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 15

Leu Ile Asn
1

<210> SEQ ID NO 16
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 16

Lys Leu Lys
1

<210> SEQ ID NO 17
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 17

Pro Leu Val
1

<210> SEQ ID NO 18
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 18

Pro Gly Met
1

<210> SEQ ID NO 19
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 19

Glu Val Ser
1

<210> SEQ ID NO 20
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 20

Phe Tyr Lys
1

<210> SEQ ID NO 21
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 21

Ile Leu Gln
1

<210> SEQ ID NO 22
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 22

Asp Pro Arg
1

<210> SEQ ID NO 23
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 23

Leu Ile Thr
1

<210> SEQ ID NO 24
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 24

Pro Leu Ala
1

<210> SEQ ID NO 25
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 25

Phe Ala Leu
1

<210> SEQ ID NO 26
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 26

Thr Ser Asp
1

<210> SEQ ID NO 27
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 27

Asn Arg Glu
1

<210> SEQ ID NO 28
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 28

Gln Val Gln
1

<210> SEQ ID NO 29
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 29

Ser Gly Leu
1

<210> SEQ ID NO 30
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 30

Arg Ile
1

<210> SEQ ID NO 31
<211> LENGTH: 143
<212> TYPE: PRT
<213> ORGANISM: Homo sapiens
```

```
<400> SEQUENCE: 31

Leu Leu Gly Gly Asp Met Val Asn Gln Ser Phe Ile Cys Asp Pro Asp
1               5                   10                  15

Asp Glu Thr Phe Ile Lys Asn Ile Ile Ile Gln Asp Cys Met Trp Ser
            20                  25                  30

Gly Phe Ser Ala Ala Ala Lys Leu Val Ser Glu Lys Leu Ala Ser Tyr
        35                  40                  45

Gln Ala Ala Arg Lys Asp Ser Gly Ser Pro Asn Pro Ala Arg Gly His
    50                  55                  60

Ser Val Cys Ser Thr Ser Ser Leu Tyr Leu Gln Asp Leu Ser Ala Ala
65                  70                  75                  80

Ala Ser Glu Cys Ile Asp Pro Ser Val Val Phe Pro Tyr Pro Leu Asn
                85                  90                  95

Asp Ser Ser Pro Lys Ser Cys Ala Ser Gln Asp Ser Ser Ala Phe
            100                 105                 110

Ser Pro Ser Ser Asp Ser Leu Leu Ser Ser Thr Glu Ser Ser Pro Gln
        115                 120                 125

Gly Ser Pro Glu Pro Leu Val Leu His Glu Glu Thr Pro Pro Thr
    130                 135                 140

<210> SEQ ID NO 32
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 32

Leu Leu Gly
1

<210> SEQ ID NO 33
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 33

Gly Asp Met
1

<210> SEQ ID NO 34
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 34

Val Asn Gln
1

<210> SEQ ID NO 35
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 35

Ser Phe Ile
1

<210> SEQ ID NO 36
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 36

Cys Asp Pro
1

<210> SEQ ID NO 37
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 37

Asp Asp Glu
1

<210> SEQ ID NO 38
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 38

Thr Phe Ile
1

<210> SEQ ID NO 39
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 39

Lys Asn Ile
1

<210> SEQ ID NO 40
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 40

Ile Ile Gln
1

<210> SEQ ID NO 41
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 41

Asp Cys Met
1

<210> SEQ ID NO 42
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 42

Trp Ser Gly
1

<210> SEQ ID NO 43
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 43

Phe Ser Ala
1

<210> SEQ ID NO 44
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 44

Ala Ala Lys
1

<210> SEQ ID NO 45
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 45

Leu Val Ser
1

<210> SEQ ID NO 46
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 46

Glu Lys Leu
1

<210> SEQ ID NO 47
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 47

Ala Ser Tyr
1

<210> SEQ ID NO 48
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 48

Gln Ala Ala
1

<210> SEQ ID NO 49
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 49

Arg Lys Asp
1

<210> SEQ ID NO 50
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 50

Ser Gly Ser
1

<210> SEQ ID NO 51
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 51

Pro Asn Pro
1

<210> SEQ ID NO 52
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 52

Ala Arg Gly
1

<210> SEQ ID NO 53
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 53

His Ser Val
1

<210> SEQ ID NO 54
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 54

Cys Ser Thr
1

<210> SEQ ID NO 55
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 55

Ser Ser Leu
1

<210> SEQ ID NO 56
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 56

Tyr Leu Gln
1

<210> SEQ ID NO 57
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 57

Asp Leu Ser
1

<210> SEQ ID NO 58
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 58

Ala Ala Ala
1

<210> SEQ ID NO 59
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 59

Ser Glu Cys
1

<210> SEQ ID NO 60
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 60

Ile Asp Pro
1

<210> SEQ ID NO 61
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 61

Ser Val Val
1

<210> SEQ ID NO 62
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 62

Phe Pro Tyr
1

<210> SEQ ID NO 63
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 63

Pro Leu Asn
1

<210> SEQ ID NO 64
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 64

Asp Ser Ser
1

<210> SEQ ID NO 65
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 65

Ser Pro Lys
1

<210> SEQ ID NO 66
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 66

Ser Cys Ala
1

<210> SEQ ID NO 67
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 67

Ser Gln Asp
1

<210> SEQ ID NO 68
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 68

Ser Ser Ala
1

<210> SEQ ID NO 69
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 69

Phe Ser Pro
1

<210> SEQ ID NO 70
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 70

Ser Ser Asp
1

<210> SEQ ID NO 71
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 71

Ser Leu Leu
1

<210> SEQ ID NO 72
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 72

Ser Ser Thr
1

<210> SEQ ID NO 73
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 73

Glu Ser Ser
1

<210> SEQ ID NO 74
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 74

Pro Gln Gly
1

<210> SEQ ID NO 75
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 75

Ser Pro Glu
1

<210> SEQ ID NO 76
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 76

Pro Leu Val
1

<210> SEQ ID NO 77
<211> LENGTH: 3
<212> TYPE: PRT
<213> ORGANISM: Artificial Sequence
<220> FEATURE:
<223> OTHER INFORMATION: Synthetic Peptide
```

```
<400> SEQUENCE: 77

Leu His Glu
1

<210> SEQ ID NO 78
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 78

Glu Thr Pro
1

<210> SEQ ID NO 79
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 79

Pro Thr Thr
1

<210> SEQ ID NO 80
<211> LENGTH: 27
<212> TYPE: DNA
<213> ORGANISM: Artificial Sequence
<220> FEATURE:
<223> OTHER INFORMATION: Synthetic PCR primer

<400> SEQUENCE: 80
ttaatagaga aacttcagtc tggaatg                                       27

<210> SEQ ID NO 81
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 81
gtggtaaagg atcagatttg tgatgtgaga                                    30

<210> SEQ ID NO 82
<211> LENGTH: 20
<212> TYPE: DNA
<213> ORGANISM: Artificial Sequence
<220> FEATURE:
<223> OTHER INFORMATION: Synthetic siRNA strand

<400> SEQUENCE: 82
uaacaaugag agcacggctt                                               20

<210> SEQ ID NO 83
<211> LENGTH: 23
<212> TYPE: DNA
<213> ORGANISM: Artificial Sequence
<220> FEATURE:
<223> OTHER INFORMATION: Synthetic siRNA strand
```

<400> SEQUENCE: 83
ccuacauccc gaucgaugau gtt                                        23

<210> SEQ ID NO 84
<211> LENGTH: 21
<212> TYPE: DNA
<213> ORGANISM: Artificial Sequence
<220> FEATURE:
<223> OTHER INFORMATION: Synthetic siRNA strand

<400> SEQUENCE: 84
cugugguugu guuugcacut t                                          21

<210> SEQ ID NO 85
<211> LENGTH: 29
<212> TYPE: DNA
<213> ORGANISM: Artificial Sequence
<220> FEATURE:
<223> OTHER INFORMATION: Synthetic Oligonucleotide probe

<400> SEQUENCE: 85
attgctcagc atcgctgtca aagaactca                                  29

<210> SEQ ID NO 86
<211> LENGTH: 21
<212> TYPE: DNA
<213> ORGANISM: Artificial Sequence
<220> FEATURE:
<223> OTHER INFORMATION: Synthetic PCR primer

<400> SEQUENCE: 86
aagctctagc ccttgcacag g                                          21

<210> SEQ ID NO 87
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 87
gtccgtgcct ctgtttcagc                                            20

<210> SEQ ID NO 88
<211> LENGTH: 26
<212> TYPE: DNA
<213> ORGANISM: Artificial Sequence
<220> FEATURE:
<223> OTHER INFORMATION: Synthetic Oligonucleotide probe

<400> SEQUENCE: 88
atgccctccc ccatgccatc ctgcgt                                     26

<210> SEQ ID NO 89
<211> LENGTH: 25
<212> TYPE: DNA
<213> ORGANISM: Artificial Sequence
<220> FEATURE:
<223> OTHER INFORMATION: Synthetic PCR primer

<400> SEQUENCE: 89
tcacccacac tgtgcccatc tacgc                                      25

```
<210> SEQ ID NO 90
<211> LENGTH: 25
<212> TYPE: DNA
<213> ORGANISM: Artificial Sequence
<220> FEATURE:
<223> OTHER INFORMATION: Synthetic PCR primer

<400> SEQUENCE: 90
cagcggaacc gctcattgcc aatgg                                          25
```